US012594390B2

(12) United States Patent
Tatkov et al.

(10) Patent No.: US 12,594,390 B2
(45) Date of Patent: Apr. 7, 2026

(54) CONTROL OF FLOW AND/OR PRESSURE PROVIDED BY BREATHING APPARATUS

(71) Applicant: Fisher & Paykel Healthcare Limited, Auckland (NZ)

(72) Inventors: Stanislav Tatkov, Auckland (NZ); Kevin Peter O'Donnell, Auckland (NZ); Sheng Feng, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/652,393

(22) Filed: Feb. 24, 2022

(65) Prior Publication Data

US 2022/0176051 A1     Jun. 9, 2022

Related U.S. Application Data

(63) Continuation of application No. 17/558,296, filed on Dec. 21, 2021, now Pat. No. 12,023,441, which is a
(Continued)

(51) Int. Cl.
*A61M 16/00*          (2006.01)
*A61B 5/00*           (2006.01)
(Continued)

(52) U.S. Cl.
CPC ......... *A61M 16/0069* (2014.02); *A61B 5/087* (2013.01); *A61B 5/091* (2013.01);
(Continued)

(58) Field of Classification Search
CPC .......... A61M 16/0069; A61M 16/0066; A61M 16/0003; A61M 16/109; A61M 16/1095;
(Continued)

(56) References Cited

U.S. PATENT DOCUMENTS 5,490,502 A    2/1996  Rapoport et al.
6,988,994 B2   1/2006  Rapoport
(Continued)

FOREIGN PATENT DOCUMENTS

WO      WO 02/26283 A2     4/2002
WO    WO 2009/146484       12/2009
(Continued)

OTHER PUBLICATIONS

Extended European Search Report issued in application No. 24167113.0 on Jun. 26, 2024.

*Primary Examiner* — Elliot S Ruddie
(74) *Attorney, Agent, or Firm* — Knobbe Martens Olson & Bear LLP

(57) ABSTRACT

The invention comprises a method of operating a breathing apparatus comprising measuring a baseline breath flow parameter being respiratory rate and/or tidal volume or a parameter derived therefrom, varying the flow rate provided by the breathing apparatus, measuring a current breath flow parameter being respiratory rate and/or tidal volume or a parameter derived therefrom, comparing the baseline and current breath flow parameters, and altering operation of the breathing apparatus based on the comparison. The invention also comprises a breathing apparatus that implements the above method.

18 Claims, 19 Drawing Sheets

Related U.S. Application Data continuation of application No. 14/402,075, filed as application No. PCT/NZ2013/000085 on May 17, 2013, now Pat. No. 11,253,663.

(60) Provisional application No. 61/648,799, filed on May 18, 2012.

(51) Int. Cl.

| | |
|---|---|
| *A61B 5/087* | (2006.01) |
| *A61B 5/091* | (2006.01) |
| *A61B 5/097* | (2006.01) |
| *A61M 16/06* | (2006.01) |
| *A61M 16/10* | (2006.01) |
| *A61M 16/16* | (2006.01) |

(52) U.S. Cl.

CPC ............ *A61B 5/097* (2013.01); *A61B 5/4812* (2013.01); *A61M 16/0003* (2014.02); *A61M 16/024* (2017.08); *A61M 16/0666* (2013.01); *A61M 16/0683* (2013.01); *A61M 16/1075* (2013.01); *A61M 16/109* (2014.02); *A61M 16/1095* (2014.02); *A61M 16/16* (2013.01); *A61M 2016/0015* (2013.01); *A61M 2016/0027* (2013.01); *A61M 2016/003* (2013.01); *A61M 2016/0039* (2013.01); *A61M 16/0066* (2013.01); *A61M 2205/52* (2013.01); *A61M 2230/40* (2013.01); *A61M 2230/42* (2013.01)

(58) Field of Classification Search

CPC ............ A61M 16/1075; A61M 16/024; A61M 16/0666; A61M 16/0683; A61M 16/16; A61M 2016/0015; A61M 2016/0027; A61M 2016/003; A61M 2016/0039; A61M 2205/52; A61M 2230/40; A61M 2230/42; A61M 16/1045; A61B 5/4806–4818; A61B 5/087; A61B 5/0878; A61B 5/091; A61B 5/097

USPC ............ 128/203.14, 203.16, 203.17, 204.14, 128/204.23, 207.17

See application file for complete search history.

(56) References Cited

U.S. PATENT DOCUMENTS

| | | | | |
|---|---|---|---|---|
| 8,789,528 | B2 | 7/2014 | Carter et al. | |
| 12,023,441 | B2 | 7/2024 | Tatkov et al. | |
| 2003/0051733 | A1 | 3/2003 | Kotmel | |
| 2005/0038353 | A1 | 2/2005 | Rapoport et al. | |
| 2005/0043652 | A1 | 2/2005 | Lovett et al. | |
| 2006/0102179 | A1* | 5/2006 | Rapoport | A61M 16/0069 |
| | | | | 128/204.22 |
| 2008/0142019 | A1* | 6/2008 | Lewis | A61B 5/0205 |
| | | | | 128/207.18 |
| 2009/0082639 | A1 | 3/2009 | Pittman et al. | |
| 2010/0252037 | A1* | 10/2010 | Wondka | A61M 16/0493 |
| | | | | 128/204.23 |
| 2011/0253136 | A1* | 10/2011 | Sweeney | A61M 16/0688 |
| | | | | 128/207.18 |
| 2011/0259334 | A1* | 10/2011 | Alfieri | A61M 16/0051 |
| | | | | 128/205.12 |
| 2012/0179061 | A1* | 7/2012 | Ramanan | A61B 5/4809 |
| | | | | 128/204.23 |
| 2013/0087143 | A1 | 4/2013 | Pujol | |
| 2014/0116440 | A1 | 5/2014 | Thompson et al. | |
| 2014/0283831 | A1 | 9/2014 | Foote et al. | |
| 2015/0128942 | A1 | 5/2015 | Tatkov et al. | |
| 2018/0325420 | A1 | 11/2018 | Gigi | |
| 2024/0299686 | A1 | 9/2024 | Tatkov et al. | |

FOREIGN PATENT DOCUMENTS

| | | | |
|---|---|---|---|
| WO | WO 2009/146484 | A1 | 12/2009 |
| WO | WO 2011/006199 | A1 | 1/2011 |
| WO | WO 2011/141843 | A1 | 11/2011 |
| WO | WO 2012/020314 | A2 | 2/2012 |
| WO | WO 2016/139645 | A1 | 9/2016 |

* cited by examiner

4a

CONTROL OF FLOW AND/OR PRESSURE PROVIDED BY BREATHING APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to a breathing apparatus including but not solely limited to breathing apparatus providing pressure therapy (such as PAP machines or similar) for treating obstructive sleep apnea and/or breathing apparatus providing flow and/or nasal high flow (NHF) therapy for various respiratory disorders.

Description of the Related Art

Breathing apparatus exist that provide flow and/or pressure therapy to a patient.

A certain level of flow and/or pressure are usually desired to provide effective therapy. However, a flow or pressure that is too high can produce undesirable effects in a patient that is awake.

It is an object of the present invention to alter the flow and/or pressure provided to a patient by a breathing apparatus dependent on whether they are awake or asleep and/or based on the reaction of breath flow parameters to changes in flow, or to overcome at least some of the drawbacks mentioned above.

SUMMARY OF THE INVENTION

In one aspect the present invention may be said to consist in a method of operating a breathing apparatus comprising the steps of providing fluid to a patient at a flow rate, measuring a current breath flow parameter of a patient, the breath flow parameter comprising respiratory rate and/or tidal volume, or one or more parameters derived therefrom, comparing the current breath flow parameter to an equivalent baseline breath flow parameter of the patient measured previously at a different baseline flow rate, altering operation of the breathing apparatus based on the comparison.

Preferably, the method further comprises determining a sleep state of a patient based on the comparison between the current and previous breath flow parameters, wherein altering operation of the breathing apparatus based on the comparison utilises the determination of sleep state.

Preferably the method further comprises the step of, prior to measuring a current breath flow parameter of a patient, increasing, decreasing or maintaining the flow rate of the fluid provided to the patient such that the flow rate is higher than the baseline flow rate.

Preferably the method further comprises the step of, prior to measuring a current breath flow parameter of a patient, increasing, decreasing or maintaining the flow rate of the fluid provided to the patient such that the flow rate is lower than the baseline flow rate.

Preferably the baseline breath flow parameter is measured during a calibration process.

Preferably wherein the baseline breath flow parameter is measured during actual use of the breathing apparatus.

Preferably if the sleep state of a patient cannot be determined then current breath flow parameter becomes a baseline breath flow parameter.

Preferably the method further comprises after the current breath flow parameter becomes the baseline breath flow parameter, measuring a current breath flow parameter of a patient, the breath flow parameter comprising respiratory rate and/or tidal volume, or one or more parameters derived therefrom, comparing the current breath flow parameter to the baseline breath flow parameter of the patient measured previously at a different baseline flow rate, altering operation of the breathing apparatus based on the comparison.

Preferably the flow rate of the fluid provided to the patient is increased, decreased or maintained but is above the baseline flow rate, the current breath flow parameter is a current respiratory rate and/or current tidal volume, the baseline breath flow parameter is a baseline respiratory rate and/or baseline tidal volume, and an awake sleep state is determined if the current respiratory rate is lower than the baseline respiratory rate, and/or the current tidal volume is higher than the baseline tidal volume.

Preferably the flow rate of the fluid provided to the patient is increased, or decreased or maintained but is above the baseline flow rate, the current breath flow parameter is a current respiratory rate and/or current tidal volume, the baseline breath flow parameter is a baseline respiratory rate and/or baseline tidal volume, and an asleep sleep state is determined if the current respiratory rate is the same as or slightly lower than the baseline respiratory rate, and/or the current tidal volume is lower than the baseline tidal volume.

Preferably the flow rate of the fluid provided to the patient is increased, decreased or maintained but is below the baseline flow rate, the current breath flow parameter is a current respiratory rate and/or current tidal volume, the baseline breath flow parameter is a baseline respiratory rate and/or baseline tidal volume, and an awake sleep state is determined if the current respiratory rate is higher than the baseline respiratory rate, and/or the current tidal volume is lower than the baseline tidal volume.

Preferably the flow rate of the fluid provided to the patient is increase, decreased or maintained but is below the baseline flow rate, the current breath flow parameter is a current respiratory rate and/or current tidal volume, the baseline breath flow parameter is a baseline respiratory rate and/or baseline tidal volume, and an asleep sleep state is determined if the current respiratory rate is the same as or slightly higher than the baseline respiratory rate, and/or the current tidal volume is higher than the baseline tidal volume.

Preferably altering operation of the breathing apparatus comprises increasing or decreasing or maintaining the flow rate provided to the patient, preferably based on the determined sleep state.

Preferably the method comprises increasing the flow rate provided to the patient if an asleep sleep state is determined, or decreasing the flow rate provided to the patient if an awake sleep state is determined.

Preferably measuring the current breath flow parameter to compare it against a baseline breath flow parameter is triggered by one or more of: time, patient physiology.

Preferably the flow rate at which the fluid is provided to a patient is provided at a fixed or varying flow rate during a breath cycle.

Preferably the fluid is provided to a patient through a patient interface with at least one nasal prong to provide air into the dead space.

In another aspect the present invention may be said to consist in a breathing apparatus to provide fluid flow to a patient comprising a blower, at least one sensor, and a controller configured to operate the blower to generate fluid flow at a flow rate to provide to a patient, measure using the sensor a current breath flow parameter of a patient using the breathing apparatus, the breath flow parameter comprising respiratory rate and/or tidal volume, or one or more parameters derived therefrom, compare the current breath flow parameter to an equivalent baseline breath flow parameter of the patient measured previously at a different baseline flow rate, alter operation of the breathing apparatus based on the comparison.

Preferably the controller is further configured to determine a sleep state of a patient based on the comparison between the current and previous breath flow parameters, wherein altering operation of the breathing apparatus based on the comparison utilises the determination of sleep state.

Preferably the controller is further configured to, prior to measuring a current breath flow parameter of a patient, increase, maintain or decrease the flow rate of the fluid provided to the patient such that the flow rate is higher than the baseline flow rate.

Preferably the controller is further configured to, prior to measuring a current breath flow parameter of a patient, increase, maintain or decrease the flow rate of the fluid provided to the patient such that the flow rate is lower than the baseline flow rate.

Preferably the baseline breath flow parameter is measured during a calibration process.

Preferably the baseline breath flow parameter is measured during actual use of the breathing apparatus.

Preferably if the sleep state of a patient cannot be determined the current breath flow parameter becomes a baseline breath flow parameter.

Preferably the controller is further configured to, after the current breath flow parameter becomes the baseline breath flow parameter, measure a current breath flow parameter of a patient, the breath flow parameter comprising respiratory rate and/or tidal volume, or one or more parameters derived therefrom, compare the current breath flow parameter to the baseline breath flow parameter of the patient measured previously at a different baseline flow rate, alter operation of the breathing apparatus based on the comparison.

Preferably the current breath flow parameter is a current respiratory rate and/or current tidal volume, the baseline breath flow parameter is a baseline respiratory rate and/or baseline tidal volume, and the controller is configured to operate the blower so that the flow rate of the fluid provided to the patient is increased, decreased or maintained but is above the baseline flow rate, and determine an awake sleep state if the current respiratory rate is lower than the baseline respiratory rate, and/or the current tidal volume is higher than the baseline tidal volume.

Preferably the current breath flow parameter is a current respiratory rate and/or current tidal volume, the baseline breath flow parameter is a baseline respiratory rate and/or baseline tidal volume, and the controller is configured to operate the blower so that the flow rate of the fluid provided to the patient is increased, or decreased or maintained but is above the baseline flow rate, and determine an asleep sleep state if the current respiratory rate is the same as or slightly lower than the baseline respiratory rate, and/or the current tidal volume is lower than the baseline tidal volume.

Preferably the current breath flow parameter is a current respiratory rate and/or current tidal volume, the baseline breath flow parameter is a baseline respiratory rate and/or baseline tidal volume, and the controller is configured to operate the blower so that the flow rate of the fluid provided to the patient is increased, decreased or maintained but is below the baseline flow rate, determine an awake sleep state if the current respiratory rate is higher than the baseline respiratory rate, and/or the current tidal volume is lower than the baseline tidal volume.

Preferably the flow rate of the fluid provided to the patient is increase, decreased or maintained but is below the baseline flow rate, the current breath flow parameter is a current respiratory rate and/or current tidal volume, the baseline breath flow parameter is a baseline respiratory rate and/or baseline tidal volume, and the controller is configure to determine an asleep sleep state if the current respiratory rate is the same as or slightly higher than the baseline respiratory rate, and/or the current tidal volume is higher than the baseline tidal volume.

Preferably altering operation of the breathing apparatus comprises the controller operating the blower to increase or decrease the flow rate provided to the patient, preferably based on the determined sleep state.

Preferably the controller operating the blower is configured to increase the flow rate provided to the patient if an asleep sleep state is determined, or decrease the flow rate provided to the patient if an awake sleep state is determined.

Preferably measuring the current breath flow parameter to compare it against a baseline breath flow parameter is triggered by one or more of time patient physiology.

Preferably the flow rate at which the fluid is provided to a patient is provided at a fixed or varying flow rate during a breath cycle.

Preferably the fluid is provided to a patient through a patient interface with at least one nasal prong to provide air into the dead space.

In one aspect the present invention may be said to consist in a method of operating a breathing apparatus to provide therapy to a patient comprising the steps of: providing fluid to a patient at a nominal flow rate, increasing the flow rate of the fluid provided to the patient, determining a sleep/awake state of the patient from the respiratory rate and/or tidal volume at the first flow rate, if the patient is asleep, providing an fluid flow rate to the patient higher than the nominal flow rate.

Preferably increasing the fluid flow rate comprises: increasing the fluid flow rate to a fixed higher flow rate than the nominal flow rate, or ramping the fluid flow rate at a first ramp rate.

Preferably providing a fluid flow rate to the patient higher than the nominal flow rate comprises: increasing the fluid flow rate to a fixed higher flow rate than the nominal flow rate, or ramping the fluid flow rate at a second ramp rate higher than the first ramp rate.

Preferably onset of the awake/sleep state is determined by: comparing the respiratory rate and/or tidal volume to a baseline respiratory rate and/or tidal volume, wherein: an decrease in respiratory rate and/or increase in tidal volume against the baseline indicates an awake state, no change in the respiratory rate and/or a decrease in tidal volume against the base line indicates a sleep state.

In another aspect the present invention may be said to consist in a breathing apparatus to provide therapy to a patient comprising a flow generator and optionally a humidifier operated by a controller for delivering fluid flow to a patient, the controller for operating the apparatus to: provide fluid to a patient at a nominal flow rate, increase the flow rate of the fluid provided to the patient, determine a sleep/awake state of the patient from the respiratory rate and/or tidal volume at the first flow rate, if the patient is asleep, provide an fluid flow rate to the patient higher than the nominal flow rate.

Preferably increasing the fluid flow rate comprises: increasing the fluid flow rate to a fixed higher flow rate than the nominal flow rate, or ramping the fluid flow rate at a first ramp rate.

Preferably providing a fluid flow rate to the patient higher than the nominal flow rate comprises: increasing the fluid flow rate to a fixed higher flow rate than the nominal flow rate, or ramping the fluid flow rate at a second ramp rate higher than the first ramp rate.

Preferably onset the awake/sleep state is determined by: comparing the respiratory rate and/or tidal volume to a baseline respiratory rate and/or tidal volume, wherein: a decrease in respiratory rate and/or increase in tidal volume against the baseline indicates an awake state, no change in the respiratory rate and/or a decrease in tidal volume against the base line indicates a sleep state.

BRIEF DESCRIPTION OF THE DRAWINGS

Preferred embodiments of the invention will be described with reference to the following drawings of which.

DETAILED DESCRIPTION OF THE PREFERRED EMBODIMENT

In the present specification, breathing apparatus (also termed breath system or respiratory assistance apparatus/ system) can mean among other things an apparatus for providing flow therapy or an apparatus for providing pressure therapy.

Brief Description of Breathing Apparatus

Breathing apparatus for providing humidified and heated gases to a patient (either as flow or pressure therapy for example as CPAP for treating OSA or flow therapy for treating chronic respiratory disorders) for therapeutic purposes are well known in the art. Systems for providing therapy of this type (for example respiratory humidification) typically have a structure where gases are delivered to a humidifier chamber from a gases source, such as a blower (also known as a compressor, an assisted breathing unit, a fan unit, a flow generator or a pressure generator). A controller (processor) controls operation of the apparatus. It can have access to an internal or external memory that stores instructions and/or data. As the gases (fluid) pass over the hot water, or through the heated and humidified air in the humidifier chamber, they become saturated with water vapour. The heated and humidified gases are then delivered to a user or patient downstream from the humidifier chamber, via a gases conduit and a user interface. A breathing apparatus to provide flow therapy controls the flow rate of air/oxygen to the patient. A breathing apparatus to provide pressure therapy controls the pressure provided to the patient.

Figure 1A:
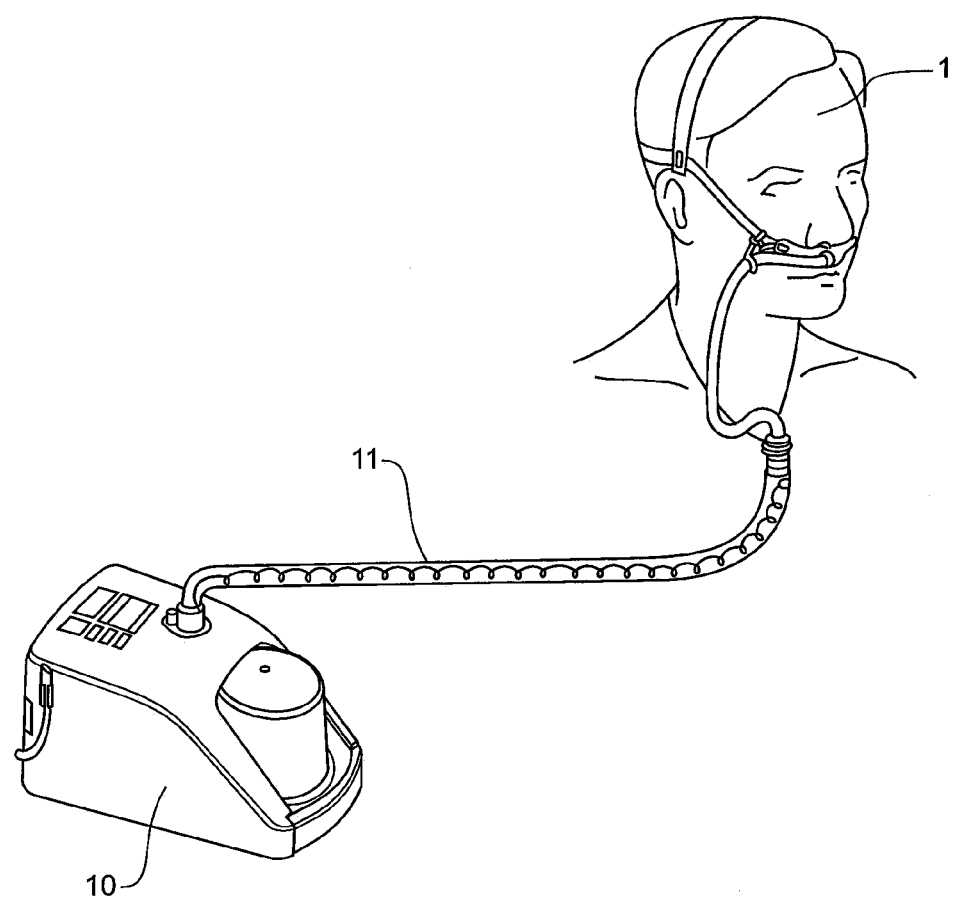
FIG. 1a shows a flow therapy breathing apparatus.
Figure 1B:
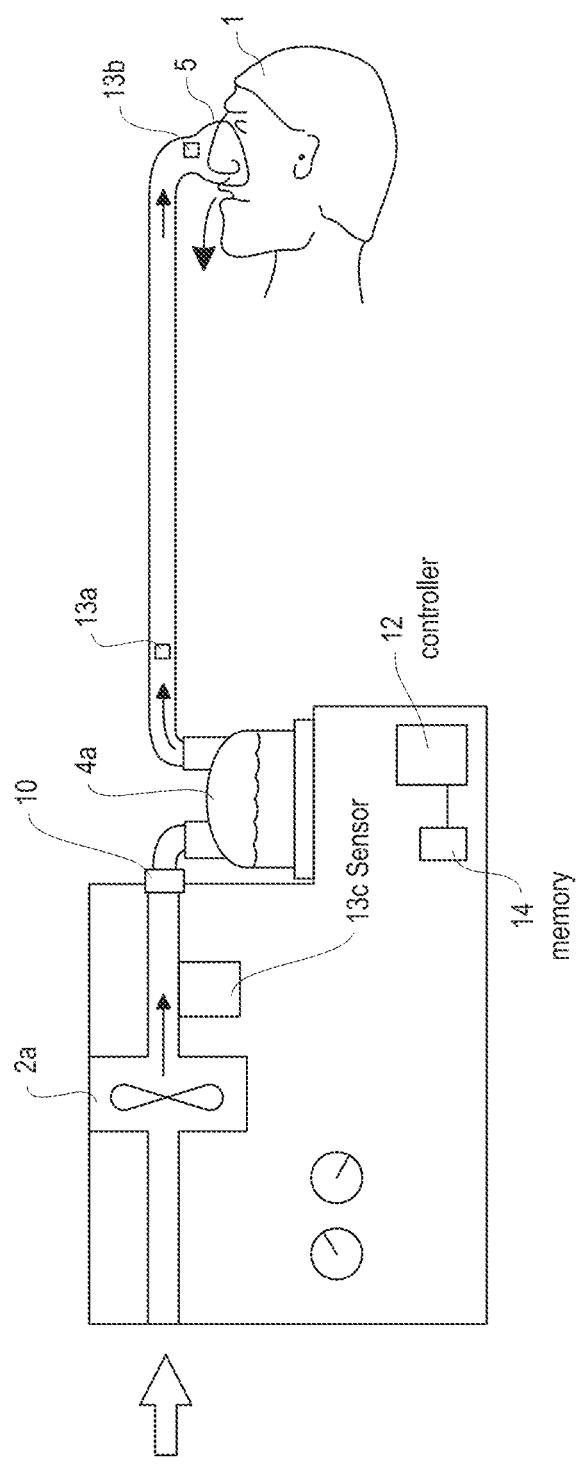
FIG. 1b shows in schematic form the components of the breathing apparatus in FIG. 1.
Figure 2:
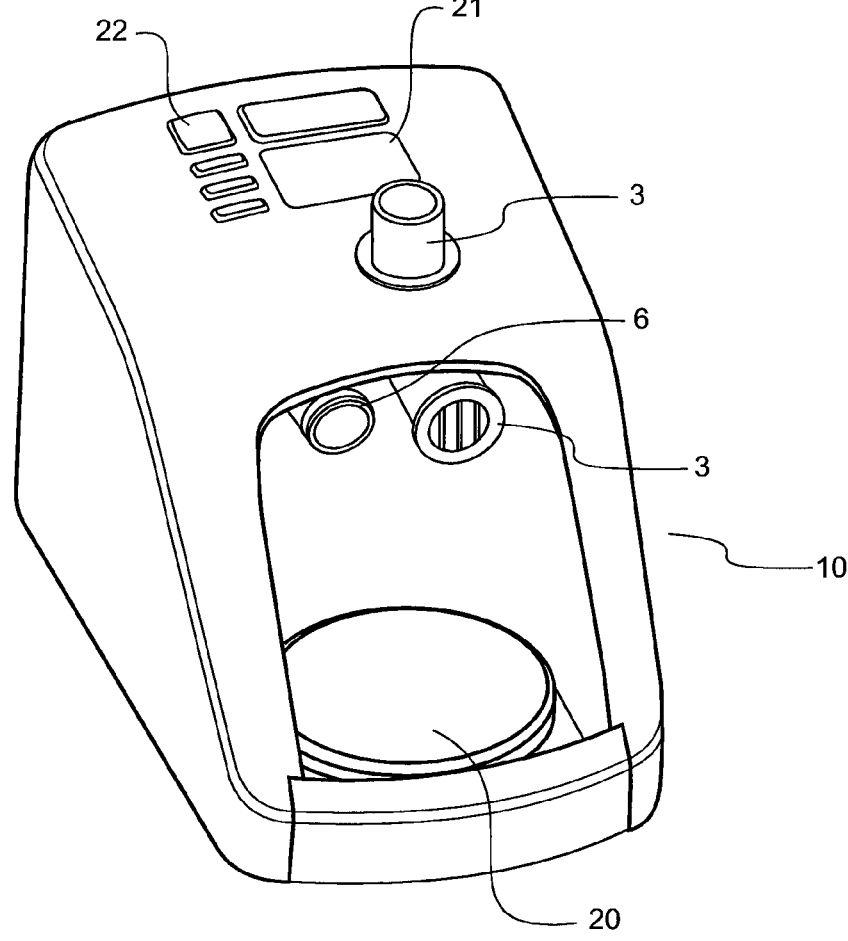
FIG. 2 shows a high flow breathing apparatus with the humidifier removed.

FIGS. 1a, 1b and 2 show a breathing apparatus for providing flow therapy and/or humidification therapy for treating respiratory disorders. In one form, such breathing apparatus can be modular and comprise a humidifier unit and a blower unit that are separate (modular) items. The modules are connected in series via connection conduits to allow gases to pass from the blower unit to the humidifier unit. In another embodiment, the blower unit and humidifier unit are integrated ("integrated unit"). In either case, a flow of air (and optionally oxygen) (more generally "fluid flow") is provided by a blower unit through a humidification chamber and then through a conduit and patient interface so that the humidified flow is provided to a patient.

FIGS. 1a, 1b and show a schematic view of an integrated unit. A user 1 receives a stream of heated and humidified air/oxygen (fluid) 11 from a breathing apparatus 10. Air/oxygen flow is provided from blower unit 2a via a connector conduit 10 to a humidifier 4a. The stream of humidified and heated air exits the humidification chamber 4a via a user conduit 3, and is provided to the patient or user 1 via a user interface 5. The process is controlled by a controller 12, which includes operating the blower to provide the required flow rate of air, operating the humidifier to create the required humidity and/or any other operations. The controller can control the blower to provide fluid flow at a fixed or varying rate during the breathing cycle. The apparatus can also have sensors 13a, 13b, 13c such as pressure and/or flow sensors for detecting operation of the apparatus and breathing of the patient. These can be on the apparatus itself or on the user (patient) interface or both. If on the interface, they can be in any suitable location such as on nasal prongs. These sensors can be used (among other things) to measure or determine respiratory rate and/or tidal volume of breath or parameters derived therefrom. The controller can control operations of the respective breathing apparatus including fan speed, humidification and other operations of the breathing apparatus such as control based on feedback from sensors 13a, 13b, 13c and recordal of compliance or other operation or sensor data onto a memory 14.

The chamber can be slid on and off. FIG. 2 shows the humidifier chamber removed, exposing a heater place 20 and the inlet 6 and outlet 3 to/from the humidifier chamber. User controls 22 and user I/O 21 are also shown.

Figure 13:
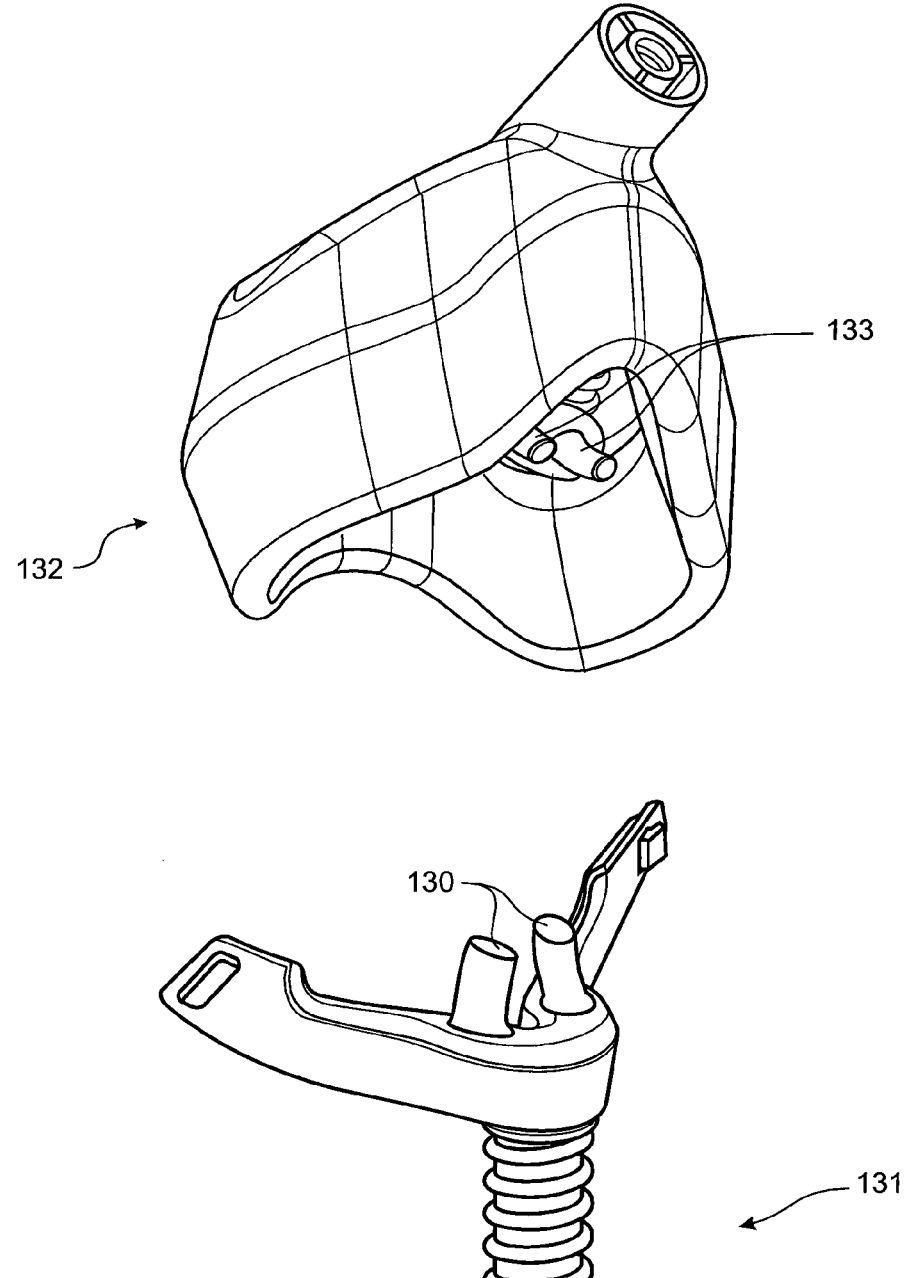
FIG. 13 shows other possible patient interfaces that could be used in the invention.

The user interface 5 shown in FIGS. 1a, 1b a nasal cannula and nasal mask respectively, by way of example. However, it should be noted that in systems of these types, a mask that covers the mouth and nose, a full-face mask, a nasal pillow mask, or any other suitable user interface could be substituted for the nasal mask shown. A mouth-only interface or oral mask, or a combination of cannula with a nasal/oral/full face mask could also be used. A hybrid mask 132 with a face mask and one or more nasal prongs 133 could be used also (see e.g. FIG. 13), or any other NHF or other interface that provides one or more prongs for jetting air. FIG. 13 also shows a patient interface 131 that has prongs 130. Sensors can be placed in or near the prongs to measure breathing parameters. Also, the patient or user end of the conduit can be connected to a tracheostomy fitting, or an endotracheal intubation. Examples of other masks are shown in FIG. 13, although these are exemplary only and not limiting. Having at least one nasal prong is particular useful although not necessarily essential for directing air into the nasal cavity to clear the dead space. This mechanism is useful for the invention as described later. Note, the term breathing apparatus is understood to refer to an apparatus (blower and/or humidifier and associated components) with or without a patient interface connected to the apparatus.

For these integrated systems, the most common mode of operation as controlled by the controller is as follows: air is drawn by the blower 2a through an inlet into the casing which surrounds and encloses at least the blower portion of the system. The blower generates an air stream from the flow generator outlet and passes this into the humidifier chamber 4a. The air stream is heated and humidified in the humidifier chamber, and exits the humidifier chamber via an outlet 3. A flexible hose or conduit 3 is connected either directly or indirectly to the humidifier outlet, and the heated, humidified gases are passed to a user 1 via the conduit. This is shown schematically in FIG. 2.

In both modular and integrated systems, the gases provided by the blower unit are generally sourced from the surrounding atmosphere. However, some forms of these systems may be configured to allow a supplementary gas (e.g. oxygen) to be blended with the atmospheric air for particular therapies. In such systems, a gases conduit supplying the supplemental gas is typically either connected directly to the humidifier chamber or elsewhere on the high pressure (flow outlet) side of the blower unit, or alternatively to the inlet side of the blower unit as described in WO 2007/004898. This type of respiratory assistance system is generally used where a patient or user requires oxygen therapy, with the oxygen being supplied from a central gases source. The oxygen from the gases source is blended with the atmospheric air to increase the oxygen fraction before delivery to the patient. Such systems enable oxygen therapy to be combined with high flow humidification therapy for the treatment of diseases such as COPD. In such therapies, the oxygen fraction being delivered to the patient be known and controlled. The oxygen fraction being delivered to the patient can be manually calculated or estimated based on a printed look-up table that sets out various oxygen fractions that have been pre-calculated based on a range of oxygen flow rates supplied from the central gas source and a range of flow rates generated by the blower unit. Alternatively, the oxygen fraction can be measured with an oxygen sensor as described in the 61/620,595.

Figure 3:
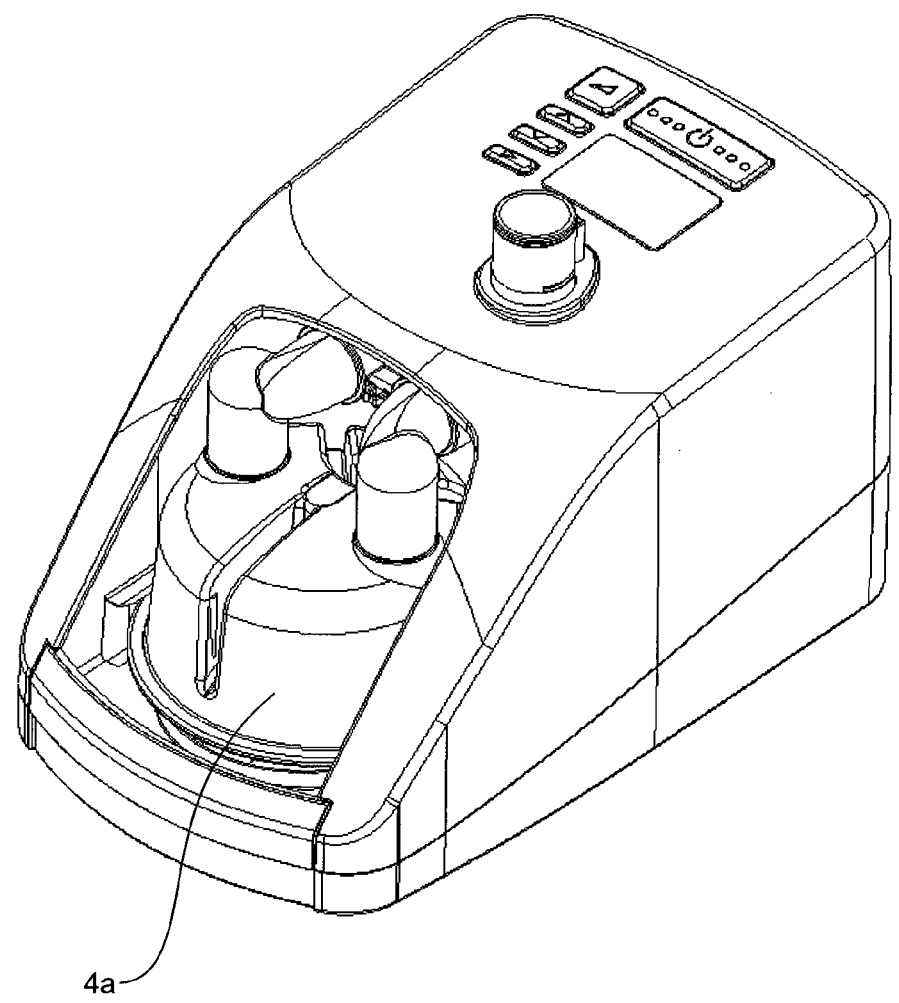
FIG. 3 shows a breathing apparatus for providing pressure therapy.
Figure 4:
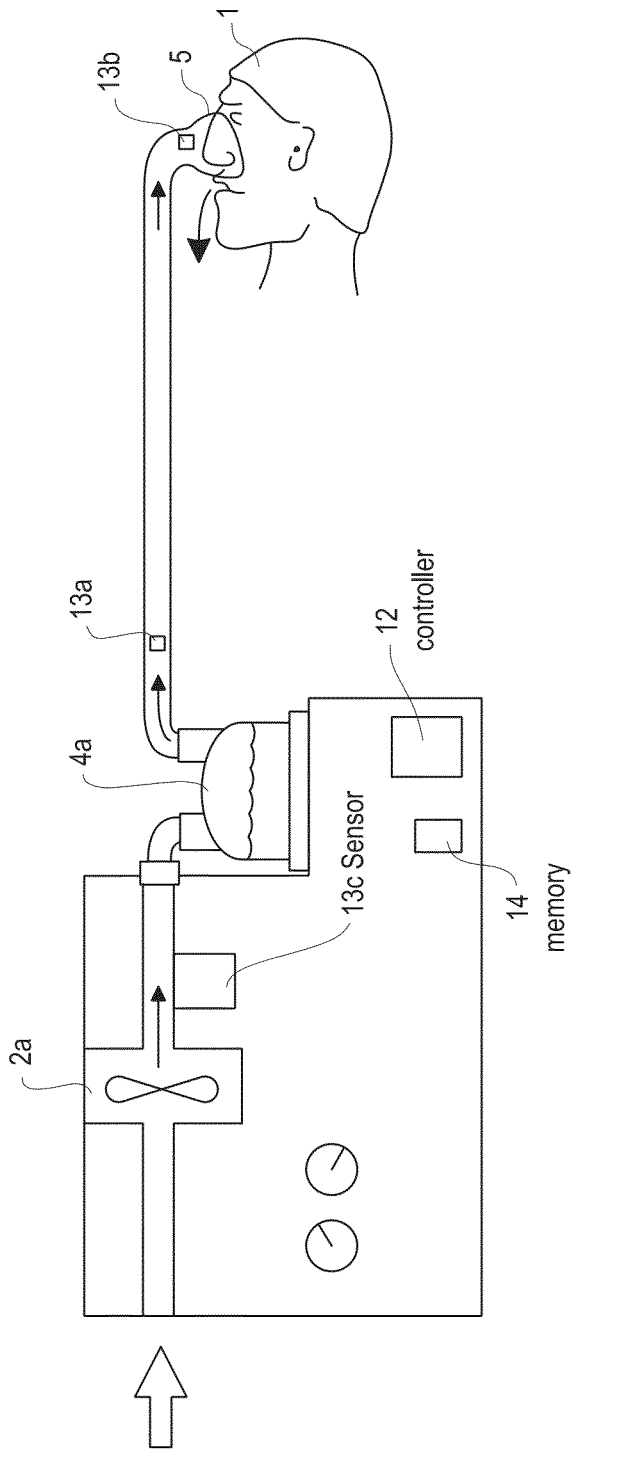
FIG. 4 shows the breathing apparatus with a humidifier in more detail.

FIGS. 3 and 4 show a breathing apparatus providing pressure therapy (such as CPAP) to treat OSA or similar. In one form, such a breathing apparatus can be modular that comprise a humidifier unit and a blower unit that are separate (modular) items. In another embodiment, the blower unit and humidifier unit are integrated ("integrated unit"). In either case, pressure is provided by a blower unit through a humidification chamber and then through a conduit and patient interface so that the humidified pressure is provided to a patient.

For example, FIG. 3 shows an integrated breathing apparatus for providing pressure therapy, e.g. a CPAP apparatus. FIG. 4 shows the components in schematic form of the integrated unit. The blower unit 2a and the humidifier unit 4a are contained within the same housing. A typical integrated system consists of a main blower unit 2a or assisted breathing unit that provides a pressurised gases flow, and a humidifier unit 4a that mates with or is otherwise rigidly connected to the blower unit. For example, the humidifier unit is mated to the blower unit by slide-on or push connection, which ensures that the humidifier unit is rigidly connected to and held firmly in place on the main blower unit. Referring to FIG. 4, a user 1 receives a stream of heated and humidified air from a modular respiratory assistance system. Pressurised air is provided from an assisted breathing unit or blower unit 2a via a connector conduit to the humidifier chamber 4a. A controller 12 is provided to control operation of the apparatus. The stream of humidified, heated and pressurised air exits the humidification chamber 4a via a user conduit 3, and is provided to the patient or user 1 via a user interface 5. The apparatus can also have sensors 13a, 13b, 13c such as pressure and/or flow sensors for detecting operation of the apparatus and breathing of the patient. These can be on the apparatus itself or on the user (patient) interface. If on the interface, they can be in any suitable location such as on nasal prongs. These sensors can be used (among other things) to measure or determine respiratory rate and/or tidal volume of breath or parameters derived therefrom. The controller can control operations of the respective breathing apparatus including fan speed, humidification and other operations of the breathing apparatus such as control based on feedback from sensor and recordal of compliance or other operation or sensor data onto a memory 14.

U.S. Pat. No. 7,111,624 includes a detailed description of an integrated system. A 'slide-on' water chamber is connected to a blower unit in use. A variation of this design is a slide-on or clip-on design where the chamber is enclosed inside a portion of the integrated unit in use. An example of this type of design is shown in WO 2004/112873, which describes a blower, or flow generator, and an associated humidifier.

Description of Operation

In a breathing apparatus that provides a flow therapy (usually NHF), generally the higher the flow rate of the air/oxygen provided to the patient, the better the therapy that is provided to them. However, while a patient is awake providing a flow rate that is too high can be uncomfortable for the patient. Also it causes turbulence in the nose during expiration, which is noisy and can prevent them from sleeping. While asleep, generally it is desirable to have a higher flow rate to improve $CO_2$ washout and also to lower the chance of obstructive events during sleep. Generally, in traditional flow therapy, a rate is set that will provide the required level of therapy, typically 10-60 Litres/min, while a keeping the flow rate as low as possible to reduce the undesirable effects, taking into account the desired awake and sleep requirements. Notwithstanding the above, in other cases, upon detecting that the patient has gone to sleep or alternatively woken up it may be desirable to vary the flow rate in some manner (e.g. by ramping at it either up or down) that is appropriate to provide a flow rate that will assist the patient in the current detected sleep/awake state. Therefore, in general terms it is desirable to vary the flow rate (or other operations of the breathing apparatus) provided to the patient based on their awake/asleep state or the change of that state.

The present invention relates to an apparatus and method of control that detects whether a patient is awake or asleep and changes therapy mode according to the sleep state. By way of an example, the apparatus controls the flow rate, temperature, humidity, or air/oxygen fraction to the patient according to their sleep state and the desired flow for such states. In an embodiment of the present invention, the apparatus is controlled to keep flow rate lower while the patient is awake, and higher while they are asleep. Other flow variations can be provided also depending on the sleep stage and breathing pattern. In general terms, the controller is programmed in a manner to be described below to carry out the detection of when a patient using the breathing apparatus is awake or asleep, and to change operation (e.g. flow rate, temperature, O2 fraction delivered) of the breathing apparatus based on whether a patient is awake or asleep.

In general terms, in accordance with the present specification, low flow air/oxygen rate (termed "low flow") can be considered anything that is not "high flow". A high flow air/oxygen rate ("high flow") can be considered any flow rate where heating and/or humidification are required for comfort and/or therapy. The transition between high flow and low flow could be anywhere between 0-60 liters per minute, depending on the application. For example, for children, a high flow might be considered to start at as low as 1-2 litres per minute. These are not fixed definitions and the delineation between low flow and high flow can be anywhere. In this specification low flow is normally used to indicate a flow rate that is lower than a high flow rate and is of a rate that is an acceptable level that does not provide too much discomfort or other discussed disadvantages to a patient when awake. High flow rate can mean any flow rate that is higher than a low flow rate and is not constrained by the requirement to reduce discomfort or other disadvantages for a patient provided by high flow. It should be noted, that if a flow rate is denoted as "higher" in this specification, that does not necessarily mean it is a high flow rate, but just a flow rate that is higher relative to another referenced flow rate.

Figure 5A:
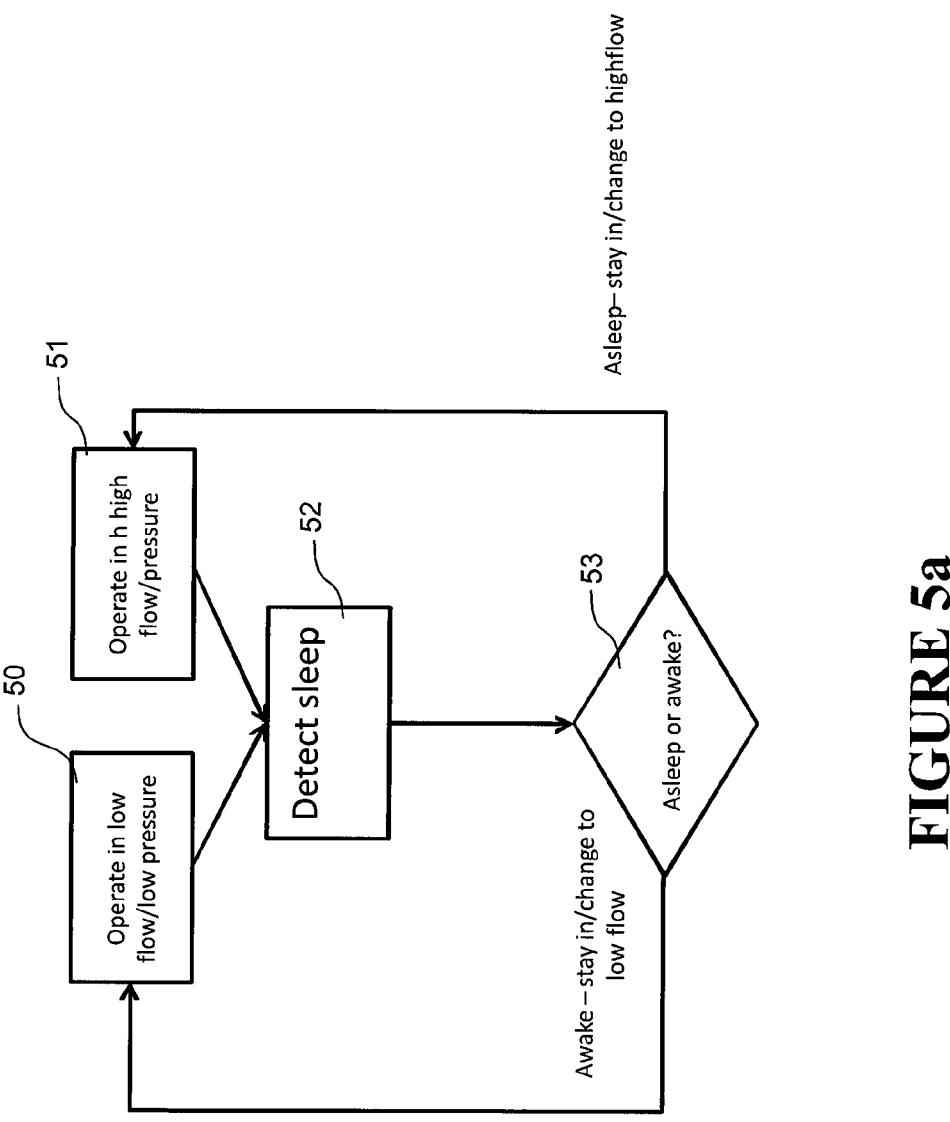
FIGS. 5a, 5b shows flow diagrams indicating a method of operating a breathing apparatus according to the invention.

FIG. 5a shows a flow diagram showing the method of operation of the breathing apparatus that provides flow therapy. The process or controller can be programmed to carry out this method. First, the controller operates the breathing apparatus to provide a nominal or typical flow rate when the patient is awake. This flow rate can be termed a "low flow rate". This flow rate can be set in the usual manner for a breathing apparatus of this nature and can be of a suitable rate to provide required therapy while still providing the desired comfort for the patient and reducing disadvantages of a high flow rate.

For paediatric patients, depending on the ages, 3-5 L/min can be considered as high flow and low flow could be any flow rate less than 3 L/min. Possible adult patient flow rates were mentioned previously.

The controller operates the breathing apparatus to provide the low flow rate preferably in this range, step 50. At a suitable point, the controller then implements the sleep state detection method, step 52. This could occur at any suitable point in the operation of the breathing apparatus, such as time based (periodically, at a particular time), or based on some physiological or other trigger (such as breathing or another "preliminary" detection routine for providing an indication of whether a patient is awake or asleep). The sleep detection process will be described below in more detail with reference to FIG. 6. If the controller determines that the patient is still awake, then the controller continues to operate the apparatus to provide the standard, nominal or low flow rate (low flow mode), step 50. If, however, the controller determines that the patient has fallen asleep, step 53, then it alters operation of the breathing apparatus. For example, the apparatus increases the flow delivered to the target (high) flow rate (high flow mode), step 51. As another example, the apparatus may also change the temperature when in sleep mode. This increased flow rate can be termed a "high flow rate" and can be, for example above 25 litres per minute.

Irrespective of whether the controller maintains the breathing apparatus in the low flow rate mode, step 50, or operates the apparatus in the high flow rate mode, step 51, the sleep detection process will be carried out again, step 52, at another suitable point based on the desired trigger. Therefore, for example, after shifting operation to the high flow mode, the controller will detect when a patient awakes again, step 52, and control operation of the breathing apparatus to return it to the low flow mode, step 50. As such, at any time during operation of the breathing apparatus it will be operated to provide low flow when the patient is asleep or high flow (or other change in operation) when the patient is awake. Clearly, there might be times before the detection algorithm operates within a low flow mode even when the patient has fallen asleep, and likewise stays in a high flow mode even though the patient has awoken as there could be some lag between changing states.

Figure 5B:
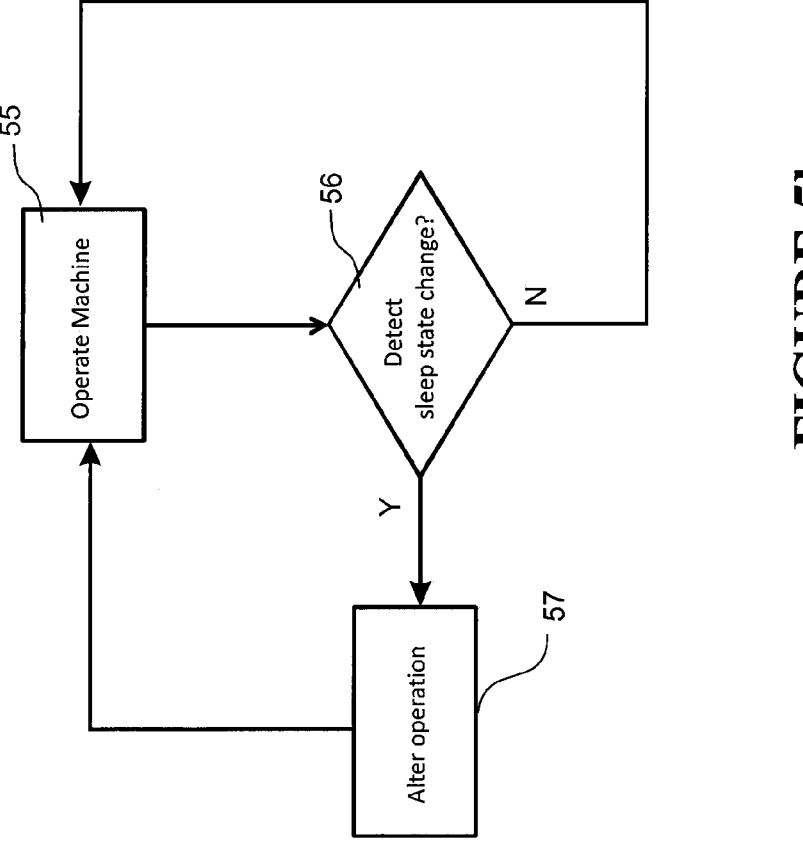

FIG. 5a shows a typical operation of the device, which commences with the patient in an awake state and the apparatus providing a nominal/low flow and then altering the flow to a high rate upon detecting sleep, or retaining the apparatus at the low/nominal flow delivery rate if the patient remains awake. FIG. 5b shows a more general operation in which the apparatus could be in any state (nominal flow or high flow delivery) and the patient could be in any state (a weight/asleep), step 55. Upon detecting a change in sleep state (according for example to FIG. 6), step 56, the flow rate is altered in any suitable manner, step 57, either up or down for either the awake or the sleep state. The shows the more general operation in which upon detecting a change in sleep state, the operation of that apparatus can be altered in any manner appropriately.

Figure 6:
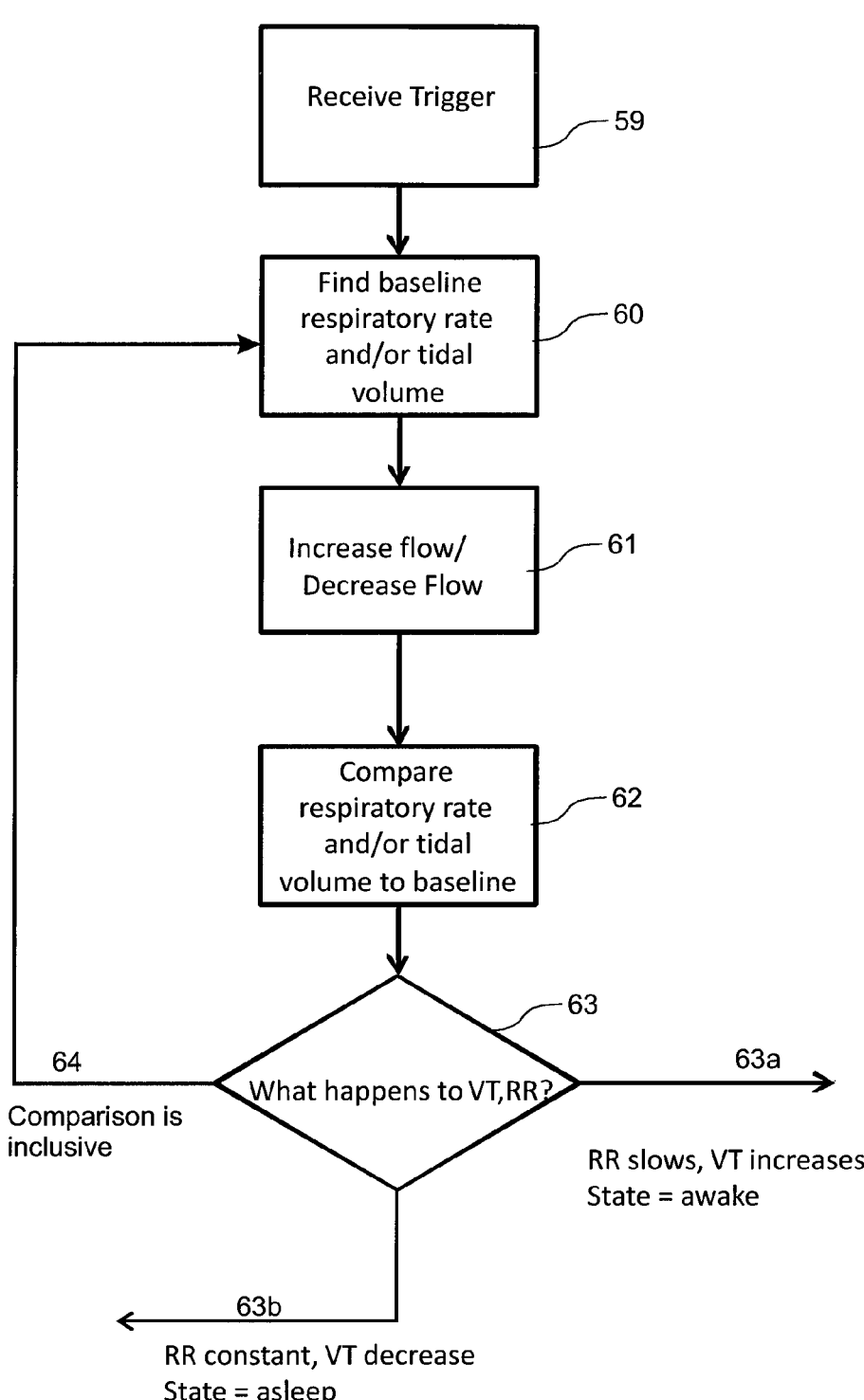
FIG. 6 shows a flow diagram of a method of detecting sleep for the purpose of operating a breathing apparatus according to the flow diagram in FIG. 5a, FIG. 7 shows a baseline respiratory rate and tidal volume of a patient at nominal flow rate.

Referring to FIG. 6, the detection process (test mode), step 52, forming part of the process of FIG. 5a is now described in further detail. The sleep detection process can be instigated by the controller at any suitable time during the operation of the breathing apparatus. For example, it may be triggered periodically e.g. every 30 minutes, or it may be triggered based on physiological data from the patient or operation data from the breathing apparatus. It could alternatively be triggered at certain times of the day. Any other possible triggers could be considered by those skilled in the art, and those mentioned should not be considered limiting. A possible trigger will be described further later.

Figure 7:
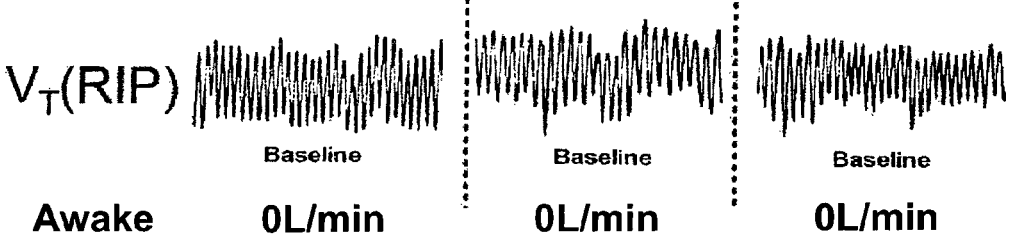

The general process for determining whether a patient is awake or asleep is based on a breathing phenomenon that has been determined by the present inventors. When a patient breathes they will have a baseline breath flow at a baseline flow rate, comprising among other things a breathing (respiratory) rate and signals indicative of tidal volume such as shown in FIG. 7. The patient will have a (different) baseline breath flow (e.g. respiratory rate and tidal volume) at a particular flow rate when they are awake and when they are asleep. FIG. 7 shows the baseline tidal volume when the patient is awake, by way of example, and it will be appreciated that a similar baseline graph could be produced for when the patient is asleep. This baseline breathing flow might be in the presence of oxygen/air flow provided at a baseline flow rate, such as a nominal rate (e.g. 15 Litres/ minute) by a breathing apparatus, or at no applied flow (that is, 0 litres/minute). The baseline breath flow parameters such as respiratory rate and tidal volume can be determined at any suitable time, such as at a particular flow rate during a calibration routine prior to actual use of the apparatus or at another time prior to actual therapeutic use of the apparatus, or the baseline breath flow parameters could be determined during actual use of the apparatus at the flow rate currently provided by the apparatus at that time. If the flow rate of air/oxygen delivered to the patient by the breathing apparatus is increased or higher than the baseline flow rate, the present inventors have determined the following. First, if the patient is awake, then the respiratory rate (breathing rate) decreases/is lower and the signals indicative of tidal volume in increases/is higher (compared to the baseline respiratory rate/signals indicative of tidal volume when the patient is awake.) Alternatively, if the patient is asleep, the breathing rate will remain the same (or possibly decrease slightly) but the signals indicative of tidal volume will decrease/be lower (compared to the baseline respiratory rate/signals indicative of tidal volume when the patient is asleep.) The respiratory rates and signals indicative of tidal volumes can be measured by the apparatus using the flow and/or pressure sensors, and this information processed by the controller. Waveforms (such as that in FIG. 7) show the respiratory rates and signals indicative of tidal volumes that can be generated from the sensor information. Any one of the sensors can be positioned within the apparatus or at/near the patient interfaces. An arrangement for sensing respiratory rates and tidal volumes is described below.

Figure 8A:
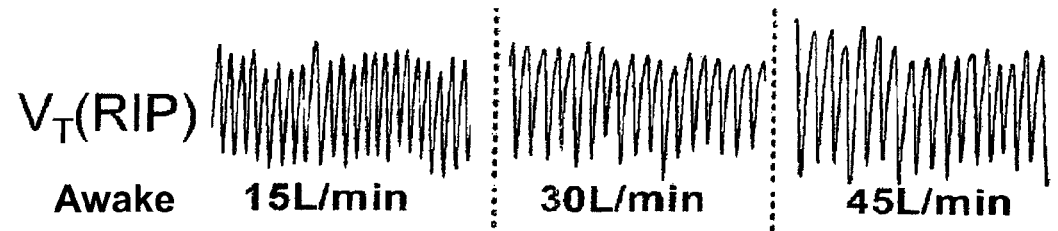
FIGS. 8a, 8c show respiratory rate and tidal volume of an awake patient when flow rates of 15 litres per minute, 30 litres per minute and 45 litres per minute are provided by the breathing apparatus.

FIG. 8*a* (and shown in more detail in FIG. 8*c*) shows schematically in a tidal volume versus time trace what happens to the respiratory rate and tidal volume of an awake patient compared to the baseline respiratory rate and tidal volume (of the patient when awake) when the breathing apparatus is controlled to deliver a higher flow rate than the baseline flow rate (in this case a nominal 0 litres/minute). In this case the higher flow rates are 15 litres per minute, 30 litres per minute and 45 litres per minute. As can be seen, at a flow rate higher than the baseline flow rate in FIG. 7, the respiratory rate is lower/decreases (time between peaks/ troughs in the trace increases) and tidal volume is higher (increases) compared to the baseline respiratory rate and tidal volume at the baseline flow rate when the patient is awake. The phenomenon is more pronounced for higher flow rates.

Figure 8B:
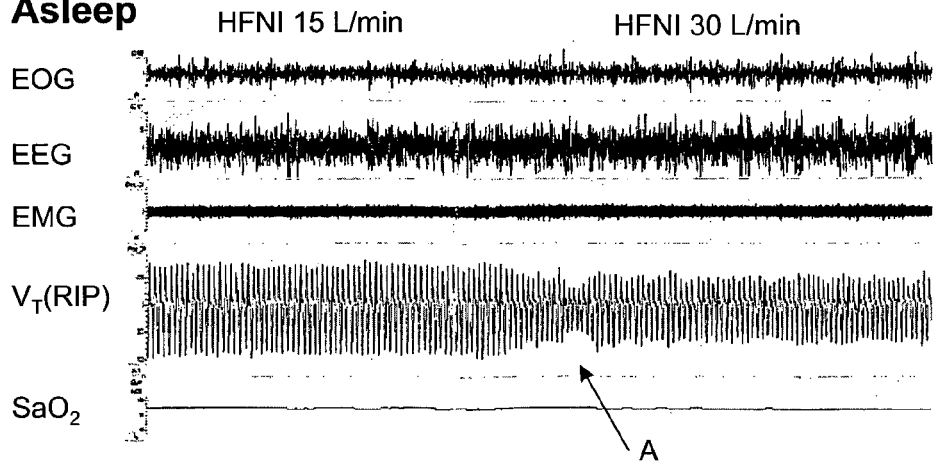
FIGS. 8b, 8d show respiratory rate and tidal volume of an asleep patient when flow rates of 15 litres per minute and 45 litres per minute are provided by the breathing apparatus.
Figure 8C:
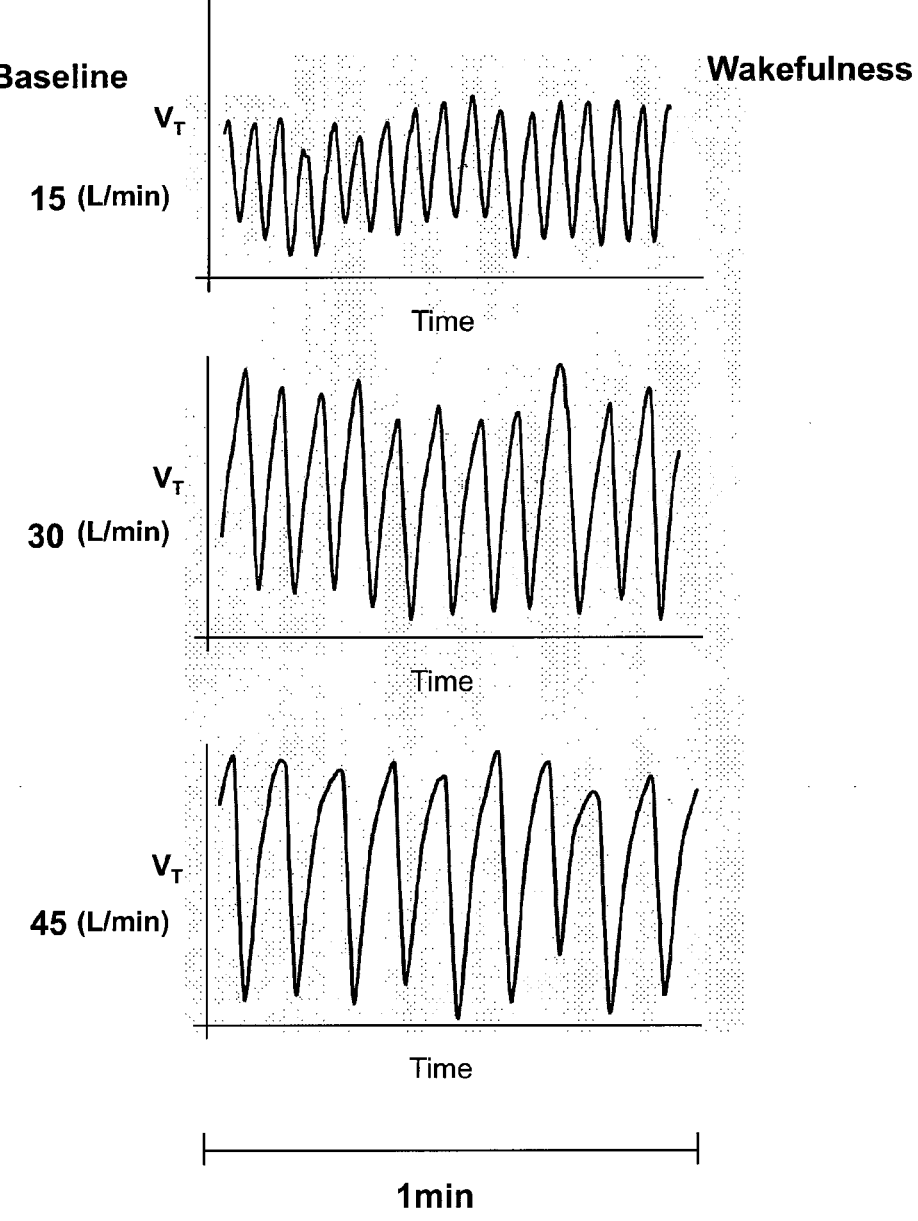
Figure 8D:
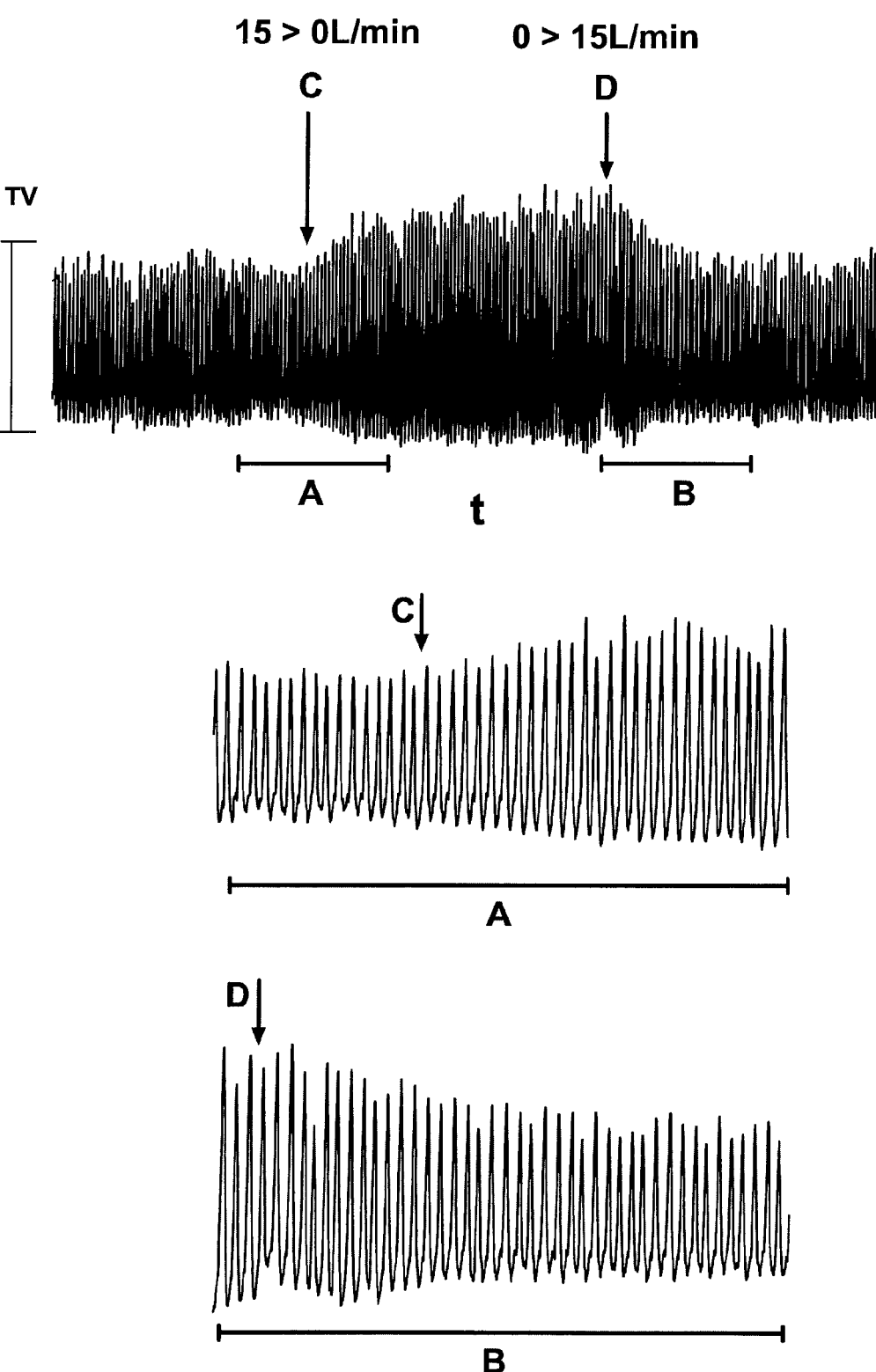
Figures 9A, 9B, 9C, 9D, 9E, 9F:
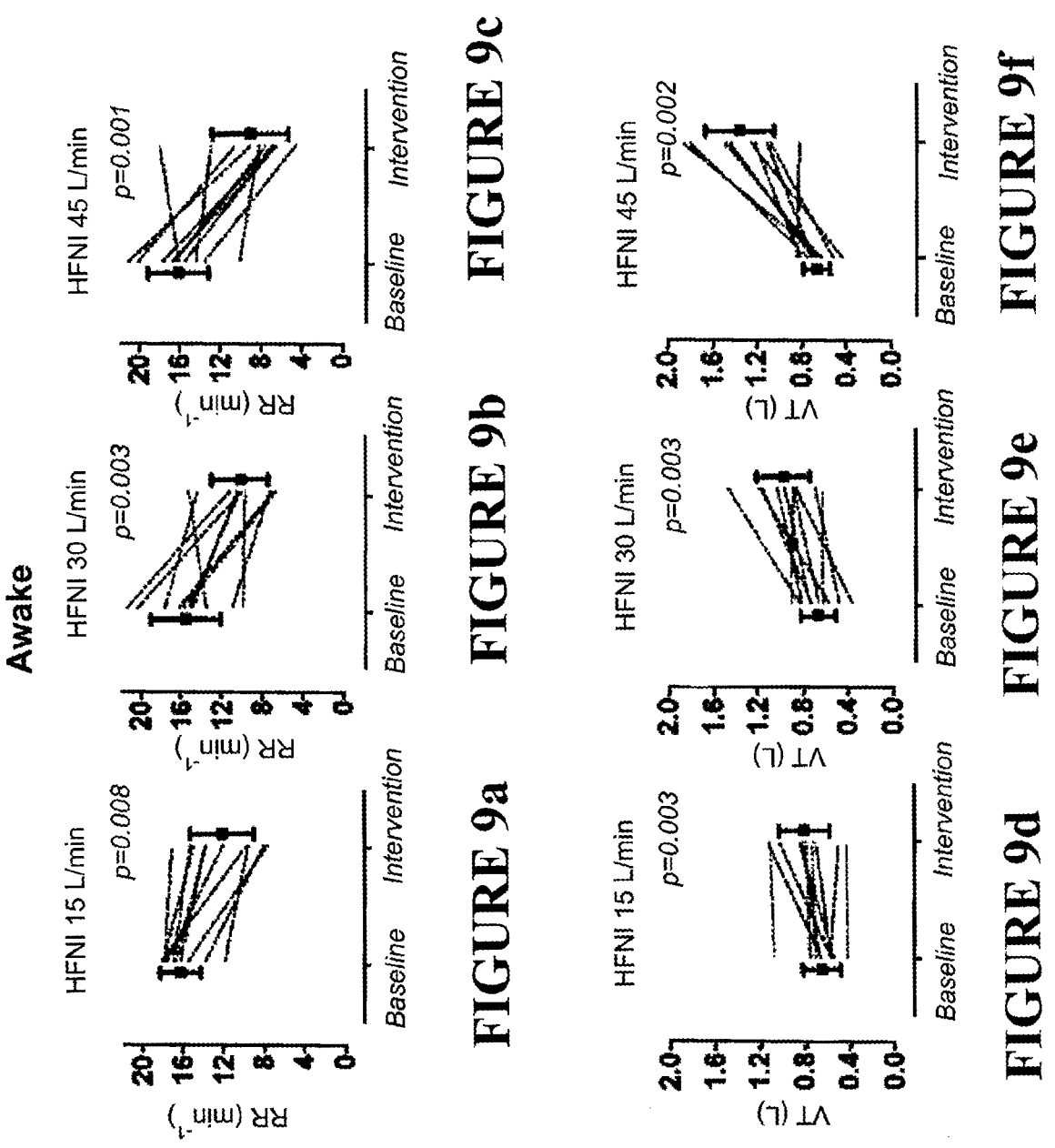
FIGS. 9A to 9F show the change in respiratory rate and tidal volume for awake patients when high flow is provided at various flow rates.
Figures 10A, 10B, 10C, 10D, 10E, 10F:
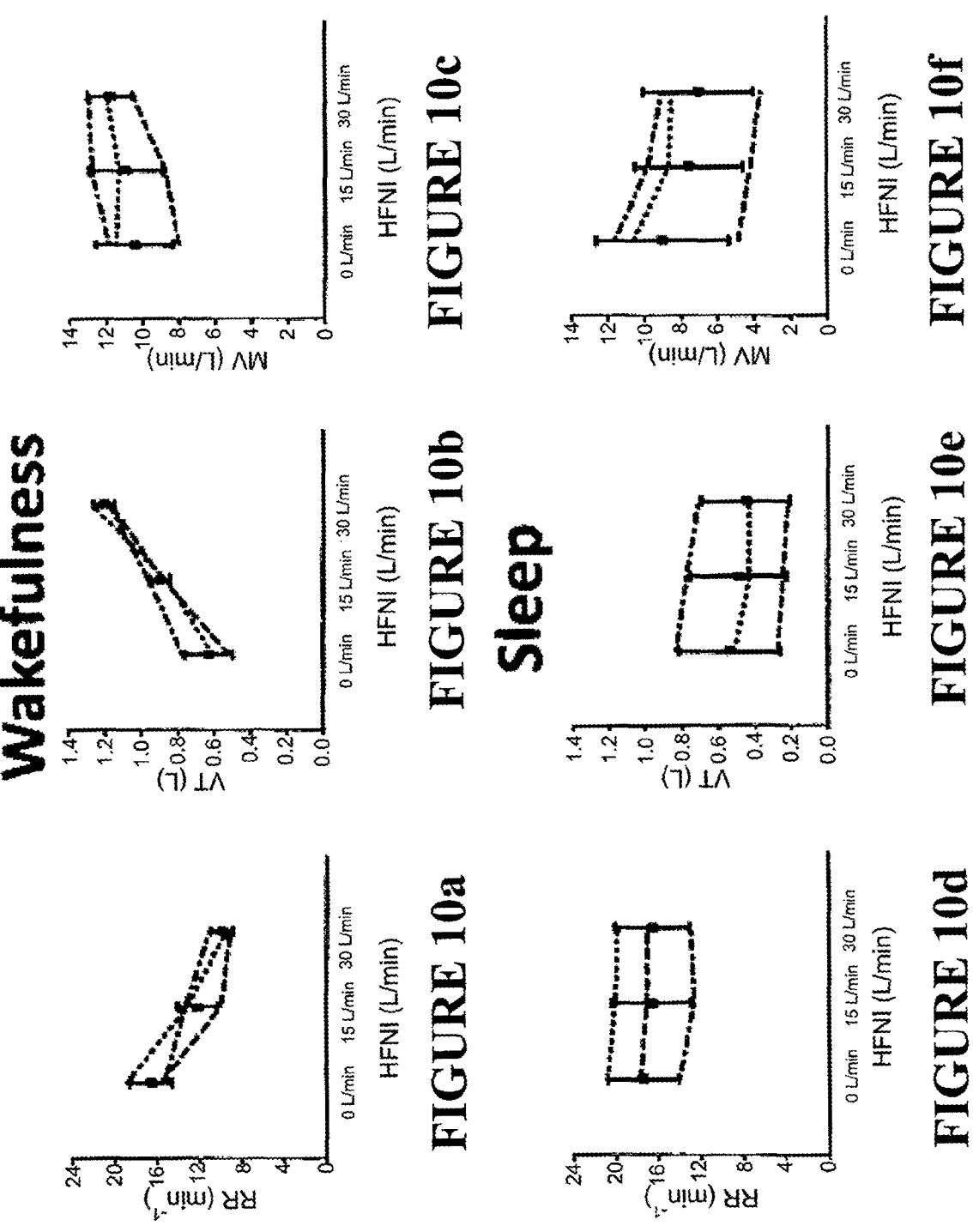
FIGS. 10A to 10F show a change in respiratory rate and title volume when high pressure is provided for awake and asleep patients.

Conversely, FIGS. 8*b* and FIG. 8*d* show what happens to the respiratory rate and tidal volume of an asleep patient compared to the baseline respiratory rate and tidal volume (when the patient is asleep) when the breathing apparatus is controlled to deliver a higher flow rate than the baseline flow rate. As can be seen in FIG. 8*b*, the flow rate increases from 15 litres per minute (baseline) to 30 litres per minute. At a flow rate higher than the baseline flow rate (transition is approximately at point A), the breathing rate stays the same (approximately—that is, the time between peaks/troughs stays approximately the same) but the tidal volume is lower (decreases) compared to the baseline respiratory rate and tidal volume at the baseline flow rate. This effect is more visible in FIG. 8*d* which shows (when the patient is asleep) the decrease of flow rate (from 15 to 0 L per minute) at point C resulting afterwards in an increase in tidal volume, and conversely an increase in flow rate at point D (from 0 to 15 L per minute) resulting in a decrease in tidal volume The phenomenon is more pronounced for higher flow rates.

Figure 14:
FIG. 14 shows the change in various breathing parameters when flow is varied when the patient is awake and asleep.

FIGS. 9*a* to 9*f* show the decrease in respiratory rate (RR) and increase in tidal volume (VT) demonstrated by an awake patient when the flow rate delivered by the breathing apparatus is increased to 15 litres per minute, 30 litres per minute and 45 litres per minute respectively over the baseline flow rate (0 litres/minute in this case) when the patient is awake. FIGS. 10*a* to 10*f* show the same phenomenon for when a patient is awake and for when they are asleep. FIG. 14 shows yet further schematic examples of other parameters and their change when flow rate increases, including Tidal volume, minute ventilation (MV) and expiratory time (TE).

FIGS. 7 to 10*f* and 14 show the change in respiratory rate and tidal volume versus a baseline respiratory rate and tidal volume (at a baseline flow rate) for a particular sleep state when a flow rate is increased from the baseline flow rate to a higher flow fate. The Figures are schematic in nature so show trends and not absolute values in all cases. It will be appreciated that the converse phenomenon will be observed if the baseline flow rate is higher than the changed flow rate. For example, a baseline respiratory rate and tidal volume could be measured for a patient (either awake or asleep) at a baseline flow rate of example 15 L per minute, and then the flow rate drop to e.g. 0 L per minute and the respiratory rate and tidal volume measured. If the respiratory rate stays same and the tidal volume increases, it is an indication that the patient is asleep. Conversely, if tidal volume decreases this can be an indication that the patient is awake. This phenomenon (e.g. looking at changes in respiratory rate and/or tidal volume when flow rate is reduced from a higher baseline flow rate to a lower flow rate) could also be used to detect changes in the sleep state of the patient.

The phenomenon occurs due to the following. Nasal High flow increases expiration resistance and decreases inspiration resistance, and it immediately slows down respiratory rate while the patient is awake. During sleep the change of resistance does not play a role any more and clearing of dead space in the nasal pharynx plays the major role in the physiological response to nasal high flow. Reduction of dead space even without increase of tidal volume can significantly decrease the dead space volume ($V_D$) to Tidal volume ($V_T$) ratio and increase ventilatory efficiency. This is the leading mechanism during sleep. During wakefulness, the increase of tidal volume apart from clearing dead space decreases the $V_D/V_T$ ratio even more significantly usually followed by a decrease of respiratory rate and as a result minute ventilation is not changed or is slightly increased. During sleep, breathing is shallow and ventilation is more efficient. Increasing flow can jet air into the dead space to flush the dead space and produce the phenomenon from which sleep state can be detected. Decreasing flow can provide the opposite effect, which can also be used to detect sleep states. Providing air via at least one nasal prong is more desirable, as it is more likely to cause the change in the dead space which produces the phenomenon, although using a patient interface with at least one nasal prong is not necessarily essential. "Dead space" as used herein can refer to both apparatus dead space and anatomical dead space. Apparatus dead space refers to zones in any additional equipment such as mask and circuits where the expired gas can be re-breathed again. Anatomical dead space comprises areas in the nose, pharynx, trachea and bronchi where $CO_2$ levels can build up. The high flow nasal interface can provide improved flushing of the anatomical dead space.

Based on the determined phenomenon, the controller of the apparatus can be programmed to carry out the sleep state detection method shown generally in FIG. 6 to determine whether the patient is awake or asleep. In one sleep state detection embodiment, first, the controller is triggered or receives an internal/external trigger to carry out a sleep/ wakefulness detection process 59. A baseline respiratory rate and tidal volume is measured for a patient for each of the awake and sleep states at a baseline flow rate. The baseline respiratory rate and tidal volume could be measured for a baseline flow rate either before operation of the apparatus during the manufacturing calibration process, or during use of the apparatus at some time prior to conducting the sleep state detection process, step 60. If the baseline breath flow parameters are measured during use of the breathing apparatus, they may actually be measured on multiple occasions, and the awake state and the sleep state baseline breathing flow parameters might be measured at different times. Where the baseline breath flow parameters are measured during use of the breathing apparatus, the baseline flow rate will be the flow rate being provided by the apparatus at the time of measurement. Baseline measurements are stored where appropriate in the controller or other memory of the apparatus. If the baseline breath flow parameters measured during a calibration process prior to use of the apparatus are used, the baseline flow rate can be a suitable nominal flow rate such as 0 litres per minute or alternatively some other low flow rate. The measurement can take place using e.g. sensors in the apparatus and/or patient interface to measure breath flow such as described below. For this embodiment, the baseline breathing flow parameters are measured during a calibration process at a nominal rate.

The breathing apparatus is then operated to increase the delivered flow rate to a higher (test mode) flow rate, step 61. This could be any suitable rate higher than the baseline flow rate, e.g. 15, 30 or 45 litres per minute or even several different rates could be applied or provided to the patient and it may not be a high flow rate. For example, if the patient is currently awake, and the apparatus is operating in the low flow mode, then the increased flow rate will be higher than the low flow rate (whatever that may be). Alternatively, if the apparatus is currently operating in a high flow mode (e.g. on the basis that previously the patient has been determined to be asleep and the flow rate increased accordingly) then the increased flow rate should be higher than that current (high flow mode) flow rate.

The controller then determines from the sensors the respiratory rate and tidal volume of the patient at the increased flow rate. This can be by way of e.g. flow and/or pressure sensors that measure the breath flow of the patient through the conduit and/or interface.

The respiratory rate and tidal volume at the elevated flow rate is then compared to the respiratory rate and tidal volume of the baseline respiratory rate and tidal volume, step 62. In making the comparison, the appropriate sleep state baseline parameter is selected (namely, the awake baseline or asleep baseline) that can be compared to the current respiratory rate and tidal volume in the current sleep state. Possibly, the baseline sleep state parameter for comparison is selected based on what the likely current sleep state is. In one alternative, an assumption can be made about the current sleep state or in another alternative a preliminary indication of the current sleep state might have been received as a result of the trigger determination. In yet another alternative, the respiratory rate and tidal volume might be compared against the baseline for both the sleep and awake state, if the actual current state cannot be assumed. If the respiratory rate is lower/decreases and/or the signals indicative of tidal volume are higher/increase (e.g. by a threshold value) in each case with respect to a wakefulness sleep state baseline respiratory rate and/or tidal volume, then the controller determines that the patient is still awake, step 63a. Alternatively, if the controller determines that respiratory rate has stayed the same (or decreased slightly) and/or the tidal volume has decreased compared to the asleep baseline respiratory rate and/or tidal volume, then the controller determines that the patient is asleep, step 63b. The processor then uses this determination in step 53 of FIG. 5a to determine further operation of the device. For example, the information is used to vary the flow rate (either up, down or kept constant) provided by the apparatus accordingly, as for example described in FIGS. 5a and 5b.

In an alternative to the embodiment above, the flow rate might not be increased during the sleep state detection process, but rather decreased (or even remain the same). If the detection flow rate is still higher than the baseline flow rate, then the same phenomenon occurs and the sleep state can be detected by comparing the current respiratory rate and/or tidal volume to the baseline respiratory rate and/or tidal volume. In an alternative, the respiratory rate and/or signals indicative of tidal volume at an increased rate could be compared against another reference, such as the respiratory rate and/or tidal volume of a patient at a particular flow rate when they are known to be awake. Here, sleep might be detected when breathing rate increases (over a slowed awake breathing rate), or expiratory time shortens. Many alternatives could be conceived also.

The description above relates to control of the apparatus based on detecting a sleep state by increasing flow rate from a lower flow rate to a higher flow rate and comparing the breath flow parameters to baseline breath flow parameters. In another sleep state detection embodiment, the detection of sleep state can be determined using the same phenomenon, but by decreasing the flow rate from the current flow rate. Referring again to FIG. 6, the alternative embodiment will be described. First, the controller is triggered to carry out a sleep/wakefulness detection process 59. A baseline respiratory rate and tidal volume is measured for a patient for each of the awake and sleep states at a baseline flow rate. The baseline respiratory rate and tidal volume could be measured for a baseline flow rate before operation of the apparatus during the manufacturing calibration process, step 60. The breathing apparatus is then operated to decrease the delivered flow rate to a lower (test mode) flow rate, step 61. This could be any suitable rate lower than the baseline flow rate, e.g. 15, 30 or 45 litres per minute or even several different rates could be applied or provided to the patient and it may not be a low flow rate.

The controller then determines from the sensors the respiratory rate and tidal volume of the patient at the increased flow rate. This can be by way of e.g. flow and/or pressure sensors that measure the breath flow of the patient through the conduit and/or interface. The respiratory rate and/or tidal volume at the elevated flow rate are then compared to the respiratory rate and/or tidal volume of the baseline respiratory rate and/or tidal volume, step 62. In making the comparison, the appropriate sleep state baseline breathing parameter is selected (namely, the awake baseline or asleep baseline) that can be compared to the current respiratory rate and tidal volume in the current sleep state.

Possibly, the baseline sleep state for comparison is selected based on what the likely current sleep state is. In one alternative, an assumption can be made about the current sleep state or in another alternative a preliminary indication of the current sleep state might have been received as a result of the trigger determination. In yet another alternative, the respiratory rate and tidal volume might be compared against the baseline for both the sleep in awake state, if the actual current state cannot be assumed. If the respiratory rate is higher or increases and/or the signals indicative of tidal volume is lower or decreases (e.g. by a threshold value) in each case with respect to a wakefulness sleep state baseline respiratory rate and/or tidal volume then the controller determines that the patient is still awake, step 63*a*. Alternatively, if the controller determines that respiratory rate has stayed the same and/or the tidal volume is higher/has increased compared to the asleep baseline respiratory rate and/or tidal volume, then the controller determines that the patient is asleep, step 63*b*. The processor then uses this determination in step 53 of FIG. 5*a* to determine further operation of the device. For example, the information is used to vary the flow rate (either up, down or kept constant) provided by the apparatus accordingly, as for example described in FIGS. 5*a* and 5B.

In an alternative, the respiratory rate and/or signals indicative of tidal volume at an increased rate could be compared against another reference, such as the respiratory rate and/or tidal volume of a patient at a particular flow rate when they are known to be awake. Here, sleep might be detected when breathing rate increases (over a slowed awake breathing rate), or expiratory time shortens. Many alternatives could be conceived also. In the embodiments described above, a preliminary test could be carried out to determine an initial indication of the sleep state and therefore which sleep state (awake or asleep) baseline breathing flow parameters are used for the comparison. For example, in the preliminary test, the current respiratory rate and/or tidal volume are measured and compared against the respiratory rate and/or tidal volume measured at a previous time. If some change in respiratory rate and/or tidal volume is apparent, then this can provide a preliminary indication of what the sleep state might be. This can the be used to select the either the baseline breathing flow parameters for an awake patient, or the baseline breathing flow parameters for the asleep patient for comparison to the measured respiratory rate and/or tidal volume during the sleep state detection method proper, which will confirm whether or not the preliminary indication is correct.

In yet another sleep state detection embodiment, a similar approach is taken to the two embodiments described above, except the baseline breath flow parameters are determined during actual use of the apparatus. Referring again to FIG. 6, first, the controller is triggered or receives an internal/external trigger to carry out a sleep/wakefulness detection process 59. A baseline respiratory rate and tidal volume is obtained by measuring the current respiratory rate and/or tidal volume at the current flow rate being provided by the apparatus, step 60. The measurement can take place using e.g. sensors in the apparatus to measure breath flow such as described below.

The breathing apparatus is then operated to increase the delivered flow rate to a higher (test mode) flow rate, step 61. This could be any suitable rate higher than the baseline flow rate (which is the previous flow rate prior to increase), e.g. 15, 30 or 45 litres per minute or even several different rates could be applied or provided to the patient and it may not be a high flow rate.

The controller then determines from the sensors the respiratory rate and tidal volume of the patient at the increased flow rate. This can be by way of e.g. flow and/or pressure sensors that measure the breath flow of the patient through the conduit and/or interface. The respiratory rate and/or tidal volume at the elevated flow rate are then compared to the respiratory rate and tidal volume of the baseline respiratory rate and/or tidal volume, step 62 (measured just before flow rate increase). The sleep state of the baseline respiratory breath flow parameters might not be known, but this is not essential. If the respiratory rate is lower/decreases and/or the signals indicative of tidal volume are higher/increases (e.g. by a threshold value) in each case with respect to baseline respiratory rate and/or tidal volume, then the controller determines that the patient is still awake, step 63*a*. Alternatively, if the controller determines that respiratory rate has stayed the same and/or the tidal volume has decreased/is lower compared to the asleep baseline respiratory rate and/or tidal volume, then the controller determines that the patient is asleep, step 63*b*. If the change in respiratory rate and/or tidal volume compared to the baseline respiratory rate and/or tidal volume is inconclusive, the process is carried out again, path 64. That is, the measured respiratory rate and/or tidal volume at the increased flow rate become the new baseline breath flow parameters, step 60. The flow rate is then increased further, step 61 and the respiratory rate and/or tidal volume as measured at that the further increased flow rate are compared against the new baseline breath flow parameters, step 62. Whether the patient is asleep or awake is determined in the same manner as described above, step 63, by looking at the change in current respiratory rate and/or tidal volume versus the baseline respiratory rate and/or tidal volume. This process continues, steps 60-63 and path 64, until there is a change in respiratory rate and/or tidal volume that is conclusive of the sleep state of the patient—be awake or asleep, step 63*a*, 63*b*. This periodic or continuous testing and further increasing of the flow rate enables the determination of the sleep state to be made, even if the sleep state changes. For example, if prior to increasing the flow rate the patient is awake and the baseline breath flow parameters are measured, but then during the testing process the patient changes state from awake to sleep, the change in parameters might be inconclusive because breathing flow parameters of an asleep state are being compared to the previous baseline breath flow parameters taken previously when the patient was awake. However, if the process is continued multiple times, such that the current breath flow parameters become the baseline parameters, the flow is increased and then new breath flow parameters measured, eventually the baseline parameters and the current measured breath flow parameters will be for the same sleep state and therefore a conclusive determination can be made by comparing them. The processor then uses this determination in step 53/56 of FIG. 5*a* or 5*b* to determine further operation of the device. For example, the information is used to vary the flow rate (either up, down or kept constant) provided by the apparatus accordingly, as for example described in FIGS. 5*a* and 5B.

In yet a further sleep state detection embodiment, the process described above could be carried out, except that rather than increasing the flow rate during the test, the flow rate is decreased so the flow rate is lower than that for the baseline breath flow parameters, step 61. If the respiratory rate is higher or increases and/or the signals indicative of tidal volume are lower or decrease by a threshold value in each case with respect to the baseline breath flow parameters, then the controller determines that the patient is still awake, step 63*a*. Alternatively, if the controller determines that respiratory rate has stayed the same and/or the tidal volume is higher/has increased compared to the baseline respiratory rate and/or tidal volume, then the controller determines that the patient is asleep, step 63*b*. If the result is inconclusive, steps 60-63 are repeated via path 64. The processor then uses this determination in step 53 of FIG. 5*a* to determine further operation of the device. For example, the information is used to vary the flow rate (either up, down or kept constant) provided by the apparatus accordingly, as for example described in FIGS. 5*a* and 5B.

Figure 11:
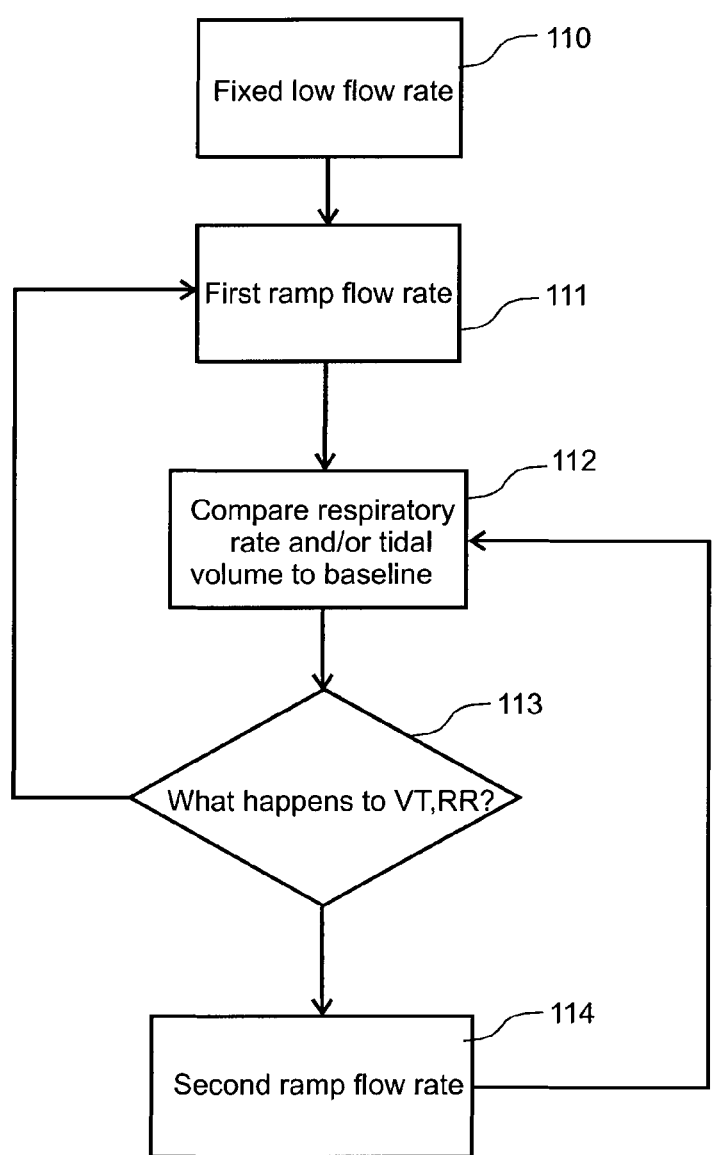
FIG. 11 shows a possible sleep/awake state detection process.

A possible embodiment of operating a breathing apparatus according to the general method described with respect to FIGS. 5*a*, 5*b*, and 6 is now described with reference to FIG. 11 which shows one possible sleep detection process in further detail. First, the process operates the breathing apparatus to provide a fixed low flow rate to the patient, step 110. At a suitable time (for example when the sleep state detection method is to start) the processor operates the breathing apparatus to increase the flow rate at a fixed (or optionally variable) rate to provide a ramp from a low flow rate to a target flow rate, step 111. This could preferably be provided over a fixed period, for example 30 minutes. Each increase during the ramp could be considered the increase in flow rate shown in step 61 in FIG. 6.

Periodically or at other suitable times or trigger points, the respiratory rate (RR) and signals indicative of tidal volume (VT) of the breath flow of the patient at the increased flow rate can be compared to the baseline respiratory rate and/or tidal volume, step 112. During the comparison step, the respiratory rate is measured. If the respiratory rate is slower than the baseline respiratory rate, then this can be a first indication that the patient is still awake. In addition or alternatively the tidal volume can be measured and compared against the baseline tidal volume. If this is higher than the baseline tidal volume, then this can be an indication that the patient is still awake. If the measured respiratory rate is the same as the baseline respiratory rate, then this can be a first indication that the patient is asleep. In addition or alternatively the tidal volume can be measured and compared against the selected baseline tidal volume. If this is lower than the selected base line tidal volume, then this can be an indication that the patient is asleep. The respiratory rate can be measured with a flow sensor and possibly the measurement improved with a flow sensor and pressure sensor. Additionally, a pressure sensor can be used to measure tidal volume. In the alternative, if the respiratory rate remains unchanged compared to the baseline, then this is an initial indication that the patient is now asleep. In addition or alternatively, tidal volume can be compared against the baseline and if it has decreased, this can be an indication that the patient is asleep.

Therefore, using one or more of the change in respiratory rate and the change in tidal volume against baseline breathing parameters, the awake or sleep state can be detected. Various combinations of comparisons could be used to detect the sleep state. For example, the current respiratory rate and tidal volume could be compared against the awake baseline respiratory rate and tidal volume and also compared against the asleep baseline respiratory rate and tidal volume, and based on the relative differences the sleep or awake state can be determined. It may be necessary to only use one of these baseline comparisons. Also, it might not be necessary to use both respiratory rate and tidal volume parameters, but just one of them. For example if the breathing rate slows with respect to the awake baseline respiratory rate then the awake state is detected and if it stays the same against the sleep baseline respiratory rate, then the sleep state is detected (compared to a baseline). Alternatively if the tidal rate increase with respect to the awake baseline tidal volume, an awake state is detected, or if it decreases compared to the baseline tidal volume, then a sleep state is detected. Other variations could be conceived.

In an alternative, the respiratory rate would be compared not to the baseline but to the awake respiratory rate. For example, if upon increasing flow rate the respiratory rate stays the same with respect to the baseline, this might mean it actually increases with respect to the awake breathing respiratory rate. Therefore if the respiratory rate increases upon increased flow, (increased flow delays expiration so usually reduces respiratory rate) this could indicate a sleep state on the assumption that prior to the increased flow there was an awake state. Similarly, a decrease in expiratory period over the low volume flow breathing could be an indication of a sleep state. Many other combinations and permutations of this are possible. It will be appreciated that it is not necessary for the tidal volume and the respiratory rate to both be considered in determining sleep state.

Once a comparison has been made and a determination has been made that the patient is in an awake state (either still or has changed state), then the ramp continues, step 111, and then comparison, step 112, 113 occurs again at the next triggered time. (Once a comparison is conducted, the measured respiratory rate and/or tidal volume become the baseline breathing parameters for the next period detection that is carried out at the next trigger point.) Alternatively, if a sleep state is detected, step 113 then the controller operates the breathing apparatus to instigate a second ramp that increases the flow rate at a higher rate than the first ramp, step 114. This is on the basis that now that the patient is asleep, it is desirable to increase the flow rate to the high rate and to do this as quickly as possible. The increase is preferably not done as a step change, so as to avoid a change that might awake the patient or otherwise provide them with discomfort. The comparison step can then continue, step 112, to check when the patient awakes again.

The above description is based on the generally assumption that operation of the apparatus starts when the patient is wake. This may or may not be the case. In fact, flow therapy can be provided continually meaning there is no defined start point where the patient is awake or asleep. Therefore, it will be apparent to those skilled in the art can relate to operation of a breathing apparatus at any point in the awake sleep cycle and the apparatus can detect sleep/awake states at any point and change operation accordingly as necessary.

Further, the above example relates to an apparatus that operates a flow rate ramp at the beginning of therapy—as one possible example. This is not limiting and is by way of example only. The sleep state detection method could be used to trigger any suitable operation/change in operation of a breathing apparatus. More generally, at any time of operation of the apparatus (either while the patient is awake or asleep and irrespective of whether the apparatus is providing therapeutic or sub-therapeutic flow) the apparatus can detect whether a patient is awake or asleep as described above and then alter the operation of the apparatus according, such as increasing or decreasing or maintaining the flow, either in therapeutic or non-therapeutic modes/flow rates. One option might be to control minute ventilation (MV) in order to achieve a reduction work of breathing. A controller would adjust the flow to maintain minimal MV. The flow setting can be predetermined in the range of e.g. 10-35 litres per minute and the controller can adjust flow depending on calculated MV.

Figure 12A:
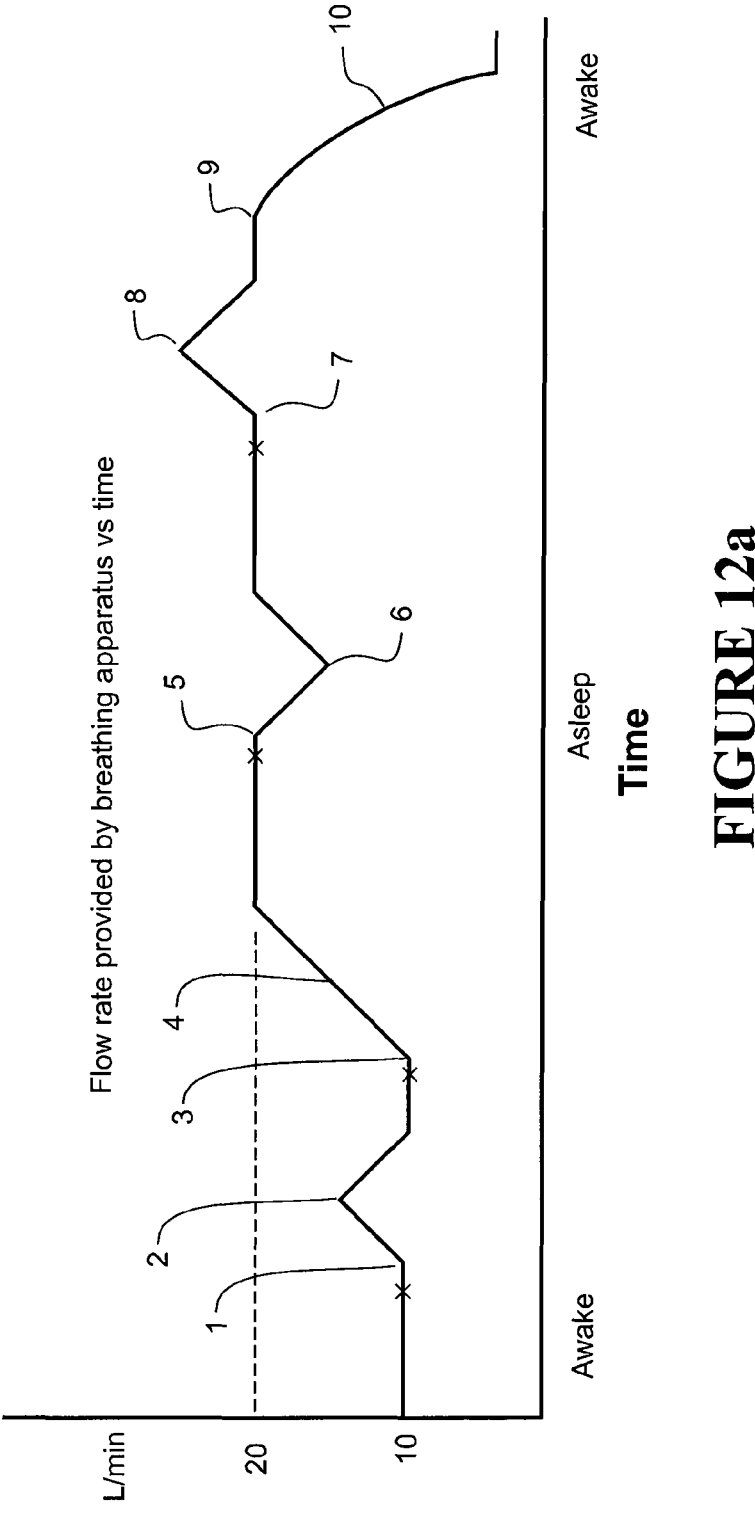
FIGS. 12a to 12c show flow traces of example detection events and resulting flow variations during operation of a breathing apparatus.
Figure 12B:
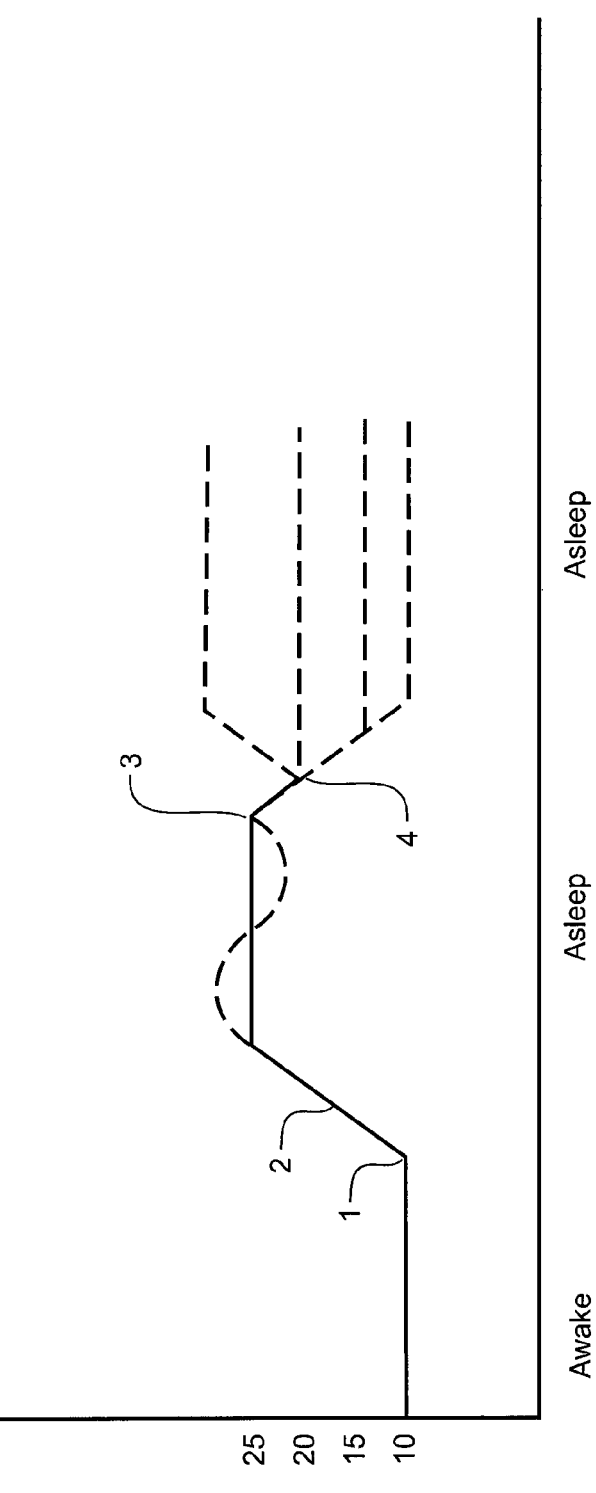
Figure 12C:
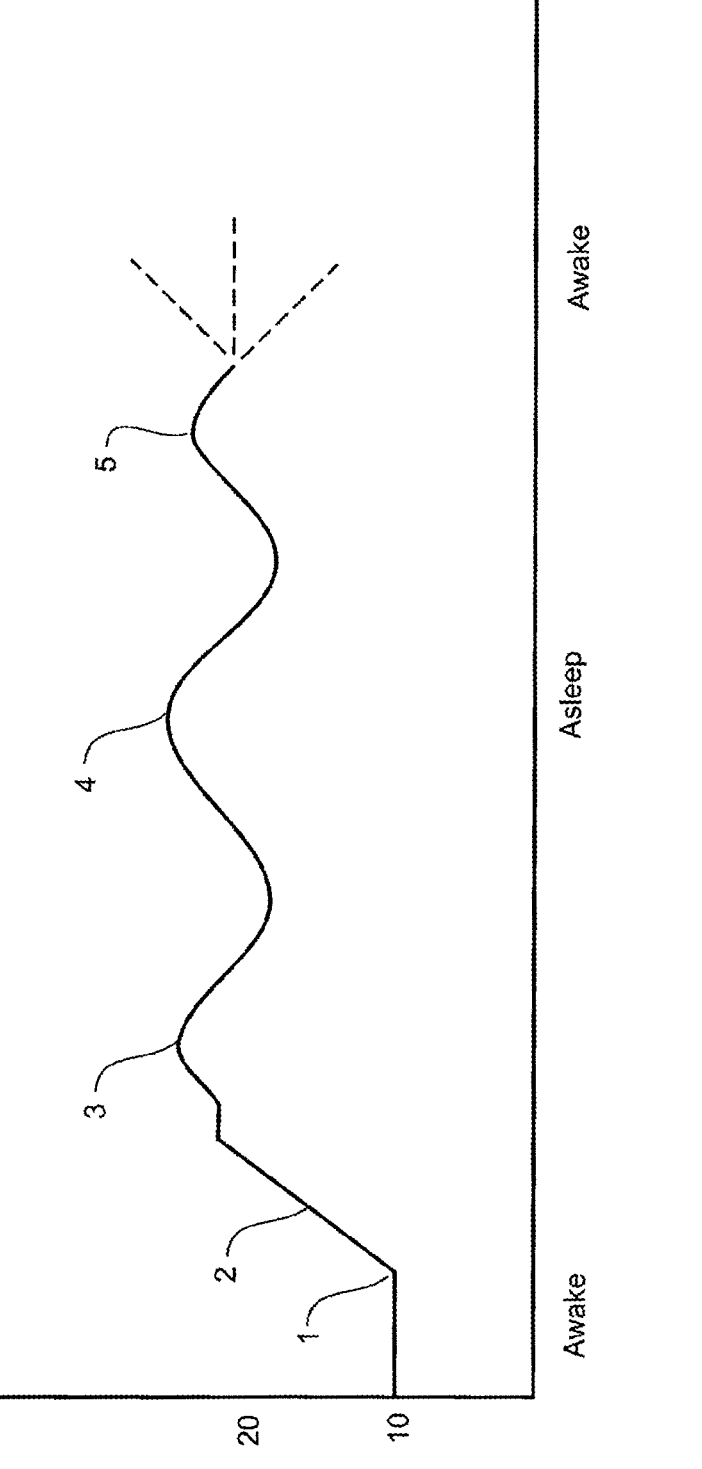

FIGS. 12*a* to 12*c* shows some more general operating events by way of example. Each figure shows the flow rate provided by the breathing apparatus to a patient and how this varies over time based on various detection events. It will be appreciated that the flow rates indicated are exemplary only and should not be considered limiting.

FIG. 12*a* shows a first flow rate trace showing various points during the operation of a breathing apparatus at which the sleep state is detected and the operation of the breathing apparatus is varied (in this case by varying of the flow rate provided). The breathing apparatus starts operation and provides an initial flow rate of 10 litres per minute, which could be sub-therapeutic and is provided while the patient is awake. At point 1, the controller of the breathing apparatus is triggered to carry out the sleep state detection method. The controller ramps up the flow rate and then at point 2 measures the respiratory rate and/or tidal volume of the patient, and then compares this to the relevant baseline respiratory rate and tidal volume of the patient. In this example, it is determined that the patient is not yet asleep and so the breathing apparatus operates to reduce the flow rate down to the initial flow rate of 10 litres per minute. Some time later, at point 3 again the breathing apparatus is triggered to carry out the detection method. It ramps the flow rate to a higher level, and then at point 4 measures the respiratory rate and/or tidal volume of the patient and compares this to the relevant baseline respiratory rate and tidal volume of the patient. In this example, the apparatus determines that the patient is now a sleep and ramps the flow rate up to the therapeutic level suitable for asleep patient, in this case 20 litres per minute. The apparatus keeps providing a flow rate at this level until it is again triggered to carry out another sleep state detection at point 5. In this case, when conducting the test, rather than increasing the flow rate further, the controller instead decreases the flow rate. At point 6 the respiratory rate and/or tidal volume is measured, and then compared against the relevant baseline respiratory rate and tidal volume. In this example, it is determined that the patient is still asleep and the flow rate is therefore returned to the therapeutic flow rate level of 20 litres per minute.

This flow rate is provided until the apparatus is again triggered to determine whether the patient is awake or asleep at point 7. In this case, by way of demonstration, the breathing apparatus increases the flow rate to carry out the test. At point 8, it is determined that the patient is still asleep, so the flow rate is returned to the therapeutic rate of 20 litres per minute and therapy continues. At point 9, the apparatus is again triggered to determine if the patient is awake or asleep, and in this case the flow level is reduced to make this determination. At point 10, the respiratory rate and/or tidal volume is measured and compared against the relevant baseline respiratory rate and tidal volume. In this case, it is determined that the patient is now awake again. As a result, the apparatus is operated to reduce the flow rate down to the sub-therapeutic level of 10 litres per minute, and the below that. FIG. 12*a* shows an example of some of the events that could occur during operation of a breathing apparatus that implements a sleep state detection method as described above and then varies its operation on the basis of the detected sleep state.

FIG. 12*b* shows a second example of an operation of breathing apparatus that utilises the detection method. The breathing apparatus initially provides a sub-therapeutic flow rate of 10 litres per minute while the patient is awake. At point 1 the apparatus is triggered to detect whether the patient is awake or asleep, and at point 2 it is determined that the patient is now asleep using the methods described above. The breathing apparatus then ramps the flow rate up to a therapeutic level of 20 litres per minute, where it continues to provide this level of flow rate until the next detection method trigger point 3. As an alternative, shown in dotted lines, the breathing apparatus might provide a varied flow rate during this period (between point 2 and point 3) as appropriate. This demonstrates that the breathing apparatus after detecting the sleep state might carry out alternative flow rate variations. At point 3, the breathing apparatus is then triggered to detect the sleep state again and lowers the flow rate as part of that detection method. At point 4, the breathing apparatus determines that the patient remains asleep. It then alters the flow rate in a suitable manner. Four possible alternatives are shown by way of example in dotted lines. In one alternative, the flow rate is increased again to a therapeutic level, but in this case higher than the previous therapeutic level to 25 litres per minute or above. In another alternative, the flow rate is maintained at the flow rate at which the detection method was carried out—15 litres per minute. In another alternative, the flow rate is reduced back down to or just above the sub-therapeutic initial level of 10 litres per minute. And in yet another alternative, the flow rate could be reduced down to a sub-therapeutic level below the initial level, such as 5 litres per minute. This figure shows that any variation of flow rate could take place following detection of the particular state.

FIG. 12*c* shows another example of a breathing apparatus operation that implements the detection method. Again the breathing apparatus operates to provide a flow rate at an initial level of 15 litres per minute. At point 1 the flow rate is increased and at point 2 the detection method is carried out to determine if the patient has gone to sleep. The controller determines that the patient has gone to sleep and increases the flow rate up to a therapeutic level of 20 litres per minute. It then varies the flow rate during this period—which could be for therapeutic reasons. Also, the varying could provide the opportunity to carry out the detection method as the increase or decrease flow rate can be used to compare the respiratory rate and tidal volume against a baseline respiratory rate and/or tidal volume—for example at point 3, 4 and 5. After point 5 it has been determined that the patient has awoken again, at which point the flow rate can be varied in a suitable manner by increasing, maintaining, or lowering the flow rate as shown in dotted lines.

In the embodiments described above, the detection method takes place by altering/varying (increasing or decreasing) the flow rate and then comparing the respiratory rate and/or tidal volume at that varied flow rate to a relevant baseline respiratory rate and/or tidal volume until a conclusive determination is made. In some embodiments, the sleep state detection method could be carried out at any flow rate, even if it is kept constant. In such a case, the respiratory rate and/or tidal volume at that constant rate could be compared against the respiratory rate and/or tidal volume for the appropriate sleep state baseline respiratory rate and/or tidal volume at a different flow rate. Also, in some embodiments the current respiratory rate and/or tidal volume as measured could be compared with that for any previous time with a different flow rate provided by the apparatus. For example, as shown in FIG. 12*c*, at point 4, a sleep state detection method could be carried out whereby the respiratory rate and tidal volume at point 4 (e.g. at 25 litres per minute) is compared to that at for example point 2 (e.g. at 15 litres per minute). The respiratory rate and tidal volume at point 2 could be used in lieu of a baseline respiratory rate and tidal volume obtained during a calibration process. The sleep state at point 2 is the same as the sleep state at point 4, the respiratory rate and/or tidal volume could be compared to that at point 2 to determine whether the patient is awake or asleep.

Many other embodiments of the invention are possible. Any arrangement of a breathing apparatus that determines sleep state by comparing the respiratory rate and/or tidal volume against a reference (baseline) respiratory rate and/or tidal volume at a reference (baseline) flow rate could be envisaged. The reference flow rate could be a baseline flow rate in which the respiratory rate and/or tidal volumes are measured during a calibration period or similar, or the reference flow rate could be at some previous flow rate provided by the breathing apparatus at some previous point during use of the breathing apparatus.

As previously described, the sleep state detection method is carried out based on a suitable trigger. One trigger could occur based on a preliminary sleep state detection method. For example, a change in respiratory rate and/or tidal volume could be determined on from that and a possible sleep state inferred. On determining a preliminary indication of sleep state change, the sleep state detection method is then triggered and could then be used to confirm the preliminary detection conclusion regarding sleep state.

The embodiments described refer to the use of respiratory rate and/or tidal volume for determining a sleep state. But any suitable breath flow parameter could be used, such a parameters derived from respiratory rate and/or tidal volume. Any embodiments above could utilise such derived parameters, with the determination of a sleep state being made based on the change of the derived parameters in a manner that could be envisage by those skilled in the art. Derived parameters could be for example: Minute ventilation (which is respiratory rate×tidal volume), expiratory time, ratio of inspiratory to expiratory time, ratio of inspiratory time to total time, ration of expiratory time to total time.

The embodiments above mention varying flow rate appropriately after detecting a sleep state. But sleep state detection could trigger other apparatus operation changes also to improve therapy.

In any of the embodiments described above, the controller operates the blower/fan to provide the required flow rate at any point to conduct the sleep state detection method, and after detection the controller operates the blower/fan and any other operations of the apparatus to provide the required flow, humidity and/or other therapy in accordance with that required by the sleep state. Operation of a breathing apparatus by a controller will be known to those in the art and is not described in detail here. The controller determines sleep state based on signals indicative of respiratory rate, tidal volume and/or any other indicative or derived parameters received from sensors that can measure appropriate parameters to provide such signals.

It will be appreciated that embodiments of the invention can comprise any method or apparatus whereby for a particular sleep state and a particular flow rate, the respiratory rate and/or tidal volume (or derived parameters) are compared to the same parameters for that sleep state at a different flow rate, and the change in those parameters can be used to determine the sleep state. Such a method or apparatus can vary the flow rate, and compare the respiratory rate and/or tidal volume or other derived parameters to those same parameters prior to varying the flow rate and from the comparison determine the sleep state.

What is claimed is:

1. A high flow therapy apparatus to provide humidified fluid flow to a patient comprising:

a housing;

a flow generator in the housing, the flow generator operative to generate fluid flow;

a humidifier operative to humidify the fluid flow;

a display on the housing;

one or more sensors in the apparatus which, in operation, measure at least one or both of pressure or flow rate; and a controller configured to:

operate, based on feedback from the one or more sensors, the flow generator and the humidifier to generate humidified fluid flow at a high flow therapy flow rate to provide to the patient, measure, using the one or more sensors, a breath flow parameter of the patient using the apparatus, the breath flow parameter comprising respiratory rate, or one or more parameters derived therefrom, select a baseline breath flow parameter from a plurality of breath flow parameters measured during a predetermined period based on an operating status of the high flow therapy apparatus, alter the operation of the flow generator to increase or decrease the high flow therapy flow rate provided to the patient based on a comparison of the baseline breath flow parameter and the measured breath flow parameter.

2. The high flow therapy apparatus of claim 1, wherein the fluid flow is provided via a nasal cannula.

3. The high flow therapy apparatus of claim 2, wherein the nasal cannula is unsealed.

4. The high flow therapy apparatus of claim 1, wherein the breath flow parameter further comprises both of the respiratory rate and a measure of tidal volume.

5. The high flow therapy apparatus of claim 4, wherein the controller is further configured to determine the respiratory rate from one or both of the flow rate or pressure of breath flow of the patient through a conduit using the one or more sensors.

6. The high flow therapy apparatus of claim 1, wherein the controller is configured to alter operation of the flow generator by controlling at least one or both of speed of a fan in the apparatus or a flow rate of the fluid flow.

7. The high flow therapy apparatus of claim 1, wherein the fluid flow is provided to the patient through a nasal cannula with at least one nasal prong to provide air into dead space of the patient.

8. The high flow therapy apparatus of claim 1, wherein the flow rate at which the fluid flow is provided to the patient is provided at varying flow rate during a breath cycle.

9. The high flow therapy apparatus of claim 1, wherein the flow rate at which the fluid flow is provided to the patient is provided at a fixed flow rate during a breath cycle.

10. The high flow therapy apparatus of claim 1, wherein in response to the patient being awake the controller is configured to increase the flow rate to lower the respiratory rate.

11. The high flow therapy apparatus of claim 1, wherein a patient interface is coupled to the humidifier via only a conduit.

12. The high flow therapy apparatus of claim 1, wherein each of the one or more sensors are located in a conduit.

13. The high flow therapy apparatus of claim 1, wherein the humidified fluid flow is provided to the patient via a conduit and the controller is further configured to measure the breath flow parameter from flow in fluid communication with the conduit.

14. The high flow therapy apparatus of claim 13, wherein the controller measures the breath flow parameter using one or more sensors located in the housing.

15. A method of controlling a high flow therapy apparatus providing humidified fluid flow to a patient, the method comprising:

operating, based on feedback from one or more sensors, a flow generator and a humidifier to generate humidified fluid flow at a high flow therapy flow rate to provide to the patient, wherein the flow generator is in a housing and configured to generate fluid flow, wherein the humidifier is configured to humidify the fluid flow;

measure, using the one or more sensors, a breath flow parameter of the patient using the apparatus, the breath flow parameter comprising respiratory rate, or one or more parameters derived therefrom, wherein the one or more sensors are in the apparatus, wherein the one or more sensors are configured to measure at least one or both of pressure or flow rate;

select a baseline breath flow parameter from a plurality of breath flow parameters measured during a predetermined period based on an operating status of the high flow therapy apparatus; and alter the operation of the flow generator to increase or decrease the high flow therapy flow rate provided to the patient based on a comparison of the baseline and a on-going breath flow parameter, wherein the humidified fluid flow is provided to the patient via a conduit, and wherein measuring the breath flow parameter of the patient comprises measuring breath flow of the patient through the conduit.

16. The method of claim 15, wherein the breath flow parameter further comprises both of the respiratory rate and a tidal volume.

17. The method of claim 16, further comprising determining the respiratory rate from one or both of the flow rate or pressure of breath flow of the patient through the conduit using the one or more sensors.

18. The method of claim 15, wherein altering operation of the flow generation comprises controlling at least one or both of speed of a fan in the apparatus or a flow rate of the fluid flow.

\* \* \* \* \*